United States Patent
Nichol et al.

(10) Patent No.: US 9,062,111 B2
(45) Date of Patent: Jun. 23, 2015

(54) CTLA-4 ANTIBODY DOSAGE ESCALATION REGIMENS

(75) Inventors: Geoffrey M. Nichol, Short Hills, NJ (US); Israel Lowy, Dobbs Ferry, NY (US)

(73) Assignee: MEDAREX, L.L.C., Princeton, NJ (US)

( * ) Notice: Subject to any disclaimer, the term of this patent is extended or adjusted under 35 U.S.C. 154(b) by 727 days.

(21) Appl. No.: 13/335,232

(22) Filed: Dec. 22, 2011

(65) Prior Publication Data

US 2012/0100101 A1    Apr. 26, 2012

Related U.S. Application Data

(63) Continuation of application No. 11/567,846, filed on Dec. 7, 2006, now Pat. No. 8,110,194.

(60) Provisional application No. 60/748,688, filed on Dec. 7, 2005.

(51) Int. Cl.
    *C07K 16/28*    (2006.01)
    *A61K 39/00*    (2006.01)

(52) U.S. Cl.
    CPC ....... *C07K 16/2818* (2013.01); *A61K 2039/505* (2013.01); *A61K 2039/545* (2013.01)

(58) Field of Classification Search
    CPC .................. C07K 16/2818; A61K 2039/505; A61K 2039/545
    USPC .................. 424/133.1, 142.1, 173.1
    See application file for complete search history.

(56) References Cited

U.S. PATENT DOCUMENTS

| | | |
|---|---|---|
| 4,399,216 A | 8/1983 | Axel et al. |
| 4,681,581 A | 7/1987 | Coates |
| 4,683,195 A | 7/1987 | Mullis et al. |
| 4,683,202 A | 7/1987 | Mullis |
| 4,735,210 A | 4/1988 | Goldenberg |
| 4,740,461 A | 4/1988 | Kaufman |
| 4,816,397 A | 3/1989 | Boss et al. |
| 4,921,040 A | 5/1990 | Ueruenduel et al. |
| 4,959,455 A | 9/1990 | Clark et al. |
| 5,101,827 A | 4/1992 | Goldenberg |
| 5,151,510 A | 9/1992 | Stec et al. |
| 5,194,594 A | 3/1993 | Khawli et al. |
| 5,434,131 A | 7/1995 | Lisley et al. |
| 5,530,101 A | 6/1996 | Queen et al. |
| 5,545,806 A | 8/1996 | Lonberg et al. |
| 5,545,807 A | 8/1996 | Surani et al. |
| 5,556,763 A | 9/1996 | Ochoa et al. |
| 5,569,825 A | 10/1996 | Lonberg et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Lonberg et al. |
| RE35,500 E | 5/1997 | Rhodes |
| 5,633,425 A | 5/1997 | Lonberg et al. |
| 5,643,763 A | 7/1997 | Dunn et al. |
| 5,648,471 A | 7/1997 | Buttram et al. |
| 5,661,016 A | 8/1997 | Lonberg et al. |
| 5,693,761 A | 12/1997 | Queen et al. |
| 5,693,792 A | 12/1997 | Torri et al. |
| 5,697,902 A | 12/1997 | Goldenberg |
| 5,703,057 A | 12/1997 | Johnston et al. |
| 5,714,350 A | 2/1998 | Co et al. |
| 5,721,367 A | 2/1998 | Kay et al. |
| 5,733,743 A | 3/1998 | Johnston et al. |
| 5,741,957 A | 4/1998 | Deboer et al. |
| 5,750,172 A | 5/1998 | Meade et al. |
| 5,756,687 A | 5/1998 | Denman et al. |
| 5,759,546 A | 6/1998 | Weinberg et al. |
| 5,770,197 A | 6/1998 | Lisley et al. |
| 5,770,429 A | 6/1998 | Lonberg et al. |
| 5,773,253 A | 6/1998 | Lisley et al. |
| 5,777,085 A | 7/1998 | Co et al. |
| 5,789,215 A | 8/1998 | Berns et al. |
| 5,789,650 A | 8/1998 | Lonberg et al. |
| 5,811,097 A | 9/1998 | Allison et al. |
| 5,814,318 A | 9/1998 | Lonberg et al. |
| 5,821,332 A | 10/1998 | Godfrey et al. |
| 5,827,690 A | 10/1998 | Meade et al. |
| 5,844,095 A | 12/1998 | Linsley et al. |
| 5,855,887 A | 1/1999 | Allison et al. |
| 5,874,299 A | 2/1999 | Lonberg et al. |
| 5,877,397 A | 3/1999 | Lonberg et al. |
| 5,885,796 A | 3/1999 | Linsley et al. |
| 5,916,771 A | 6/1999 | Hori et al. |
| 5,939,598 A | 8/1999 | Kucherlapati et al. |
| 5,968,510 A | 10/1999 | Lisley et al. |

(Continued)

FOREIGN PATENT DOCUMENTS

| | | |
|---|---|---|
| CA | 2205680 | 11/1998 |
| EP | 0 256 055 | 8/1991 |

(Continued)

OTHER PUBLICATIONS

[No authros listed] Drugs R D. 2010;10(2):97-110.*
Hainsworth, et al., "Rituximab as First-Line and Maintenance Therapy for Patients with Indolent Non-Hodgkin's Lymphona", *Journal of Clinical Oncology.*, 20(20):4261-4267 (2002).
Ansell et al., "Phase I study of ipilimumab, an anti-CTLA-4 monoclonal antibody, in patients with relapsed and refractory B-cell non-hodgkin lymphoma," *Clin. Cancer Res.* (2009);15(20):6446-6453.
Attia, et al. "Autoimmunity correlates with tumor regression in patients with metastatic melanoma treated with anti-cytotoxic T-lymphocyte antigen-4." J Clin Oncol. Sep. 1, 2005; vol. 23(25):6043-53.
Balzano, et al."CTLA-4 and CD28: similar proteins, neighbouring genes." Int J Cancer Suppl. 1992;7:28-32.
Bashey et al., "CTLA-4 blockade with ipilimumab to treat relapse of malignancy after allogeneic hematopoietic cell transplantation," *Blood* (2009);113:1581-1588.
Bashey et al., "Phase I study of a neutralizing monoclonal anti-CTLA-4 antibody (MDX-010) in patients with relapse of malignancy after allogeneic hematopoietic stem cell transplantation," *Biology of Blood and Marrow Transplantation* (2005);11(2):5.

(Continued)

*Primary Examiner* — Lynn Bristol
(74) *Attorney, Agent, or Firm* — Baker Botts L.L.P.

(57) ABSTRACT

A disease or condition, such as cancer or an infectious disease, can be treated in a patient by administering a CTLA-4 antibody in an escalating dosage regimen until a partial or complete response is elicited in the patient or a pre-determined maximum dosage is reached.

28 Claims, No Drawings

(56) References Cited

U.S. PATENT DOCUMENTS

| | | | |
|---|---|---|---|
| 5,977,318 A | 11/1999 | Lisley et al. |
| 6,051,227 A | 4/2000 | Allison et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,207,156 B1 | 3/2001 | Kuchroo et al. |
| 6,255,458 B1 | 7/2001 | Lonberg et al. |
| 6,632,927 B2 | 10/2003 | Adair et al. |
| 6,682,736 B1 | 1/2004 | Hanson et al. |
| 6,719,972 B1 | 4/2004 | Gribben et al. |
| 6,984,720 B1 | 1/2006 | Korman et al. |
| 7,034,121 B2 | 4/2006 | Carreno et al. |
| 7,229,628 B1 | 6/2007 | Allison et al. |
| 7,410,253 B2 | 8/2008 | Habermann et al. |
| 7,452,535 B2 | 11/2008 | Davis et al. |
| 7,465,446 B2 | 12/2008 | Lowy et al. |
| 7,605,238 B2 | 10/2009 | Korman et al. |
| 7,611,702 B2 | 11/2009 | Fischkoff et al. |
| 7,744,875 B2 | 6/2010 | Lowy et al. |
| 8,017,114 B2 | 9/2011 | Korman et al. |
| 8,110,194 B2 | 2/2012 | Nichol et al. |
| 8,142,778 B2 | 3/2012 | Davis et al. |
| 8,318,916 B2 | 11/2012 | Korman et al. |
| 8,784,815 B2 | 7/2014 | Korman et al. |
| 2002/0039581 A1 | 4/2002 | Carreno et al. |
| 2002/0086014 A1 | 7/2002 | Korman et al. |
| 2002/0182218 A1 | 12/2002 | Nicolette |
| 2003/0086930 A1 | 5/2003 | Mueller et al. |
| 2003/0175250 A1 | 9/2003 | Jager et al. |
| 2004/0241169 A1 | 12/2004 | Lowy et al. |
| 2005/0201994 A1 | 9/2005 | Korman et al. |
| 2005/0249700 A1 | 11/2005 | Allison et al. |
| 2006/0034844 A1 | 2/2006 | Allison et al. |
| 2007/0160619 A1 | 7/2007 | Nichol et al. |
| 2007/0248595 A1 | 10/2007 | Yang et al. |
| 2009/0074752 A1 | 3/2009 | Lowy et al. |
| 2009/0117037 A1 | 5/2009 | Davis et al. |
| 2009/0217401 A1 | 8/2009 | Korman et al. |
| 2010/0047244 A1 | 2/2010 | Korman et al. |

FOREIGN PATENT DOCUMENTS

| | | |
|---|---|---|
| EP | 0 323 997 | 4/1993 |
| EP | 0 613 944 | 9/1994 |
| EP | 0 338 841 | 3/1995 |
| EP | 0 216 846 | 4/1995 |
| EP | 0 682 039 | 11/1995 |
| EP | 0 463 151 | 6/1996 |
| EP | 0 546 073 | 9/1997 |
| EP | 1 262 193 | 12/2002 |
| WO | WO 90/04036 | 4/1990 |
| WO | WO 91/10741 | 7/1991 |
| WO | WO 92/03918 | 3/1992 |
| WO | WO 92/22645 | 12/1992 |
| WO | WO 92/22647 | 12/1992 |
| WO | WO 92/22670 | 12/1992 |
| WO | WO 93/00431 | 1/1993 |
| WO | WO 93/12227 | 6/1993 |
| WO | WO 94/02602 | 2/1994 |
| WO | WO 94/25585 | 11/1994 |
| WO | WO 94/29444 | 12/1994 |
| WO | WO 95/01994 | 1/1995 |
| WO | WO 95/03408 | 2/1995 |
| WO | WO 95/05464 | 2/1995 |
| WO | WO 95/23859 | 9/1995 |
| WO | WO 95/24217 | 9/1995 |
| WO | WO 95/33770 | 12/1995 |
| WO | WO 95/34320 | 12/1995 |
| WO | WO 96/14436 | 5/1996 |
| WO | WO 96/14865 | 5/1996 |
| WO | WO 96/22380 | 7/1996 |
| WO | WO 96/33735 | 10/1996 |
| WO | WO 96/34096 | 10/1996 |
| WO | WO 97/07671 | 3/1997 |
| WO | WO 97/13852 | 4/1997 |
| WO | WO 97/20574 | 6/1997 |
| WO | WO 97/38137 | 10/1997 |
| WO | WO 98/24884 | 6/1998 |
| WO | WO 98/24893 | 6/1998 |
| WO | WO 98/37757 | 9/1998 |
| WO | WO 98/42752 | 10/1998 |
| WO | WO 98/46996 | 10/1998 |
| WO | WO 98/50433 | 11/1998 |
| WO | WO 00/00569 | 1/2000 |
| WO | WO 00/10383 | 3/2000 |
| WO | WO 00/32231 | 6/2000 |
| WO | WO 00/37504 | 6/2000 |
| WO | WO 01/14424 | 1/2001 |
| WO | WO 03/086459 | 10/2003 |
| WO | WO 2005/003298 | 1/2005 |

OTHER PUBLICATIONS

Beck et al., "Enterocolitis in patients with cancer after antibody blockade of cytotoxic T-lymphocyte-associated antigen 4," *J Clin Oncol.* (2006);24(15):2283-9.

Beckman RA, et al., "Antibody constructs in cancer therapy: protein engineering strategies to improve exposure in solid tumors," Cancer. Jan. 15, 2007;109(2):170-9.

Bi Y, et al., "Expressions of Fas, CTLA-4 and RhoBTB2 genes in breast carcinoma and their relationship with clinicopathological factors," Zhonghua Zhong Liu Za Zhi. Oct. 2008;30(10):749-53 (Article is in Chinese, English Abstract is submitted).

Camacho et al., "Phase I/II Trial of Tremelimumab in patients with metastatic melanoma," *J. Clin. Oncol.* (2009);27:1075-1081.

Camacho et al., "Phase 1 clinical trial of anti-CTLA4 human monoclonal antibody CP-675,206 in patients (pts) with advanced solid malignancies," *J. Clin. Oncol.* 2004 ASCO Annual Meeting Proceedings (Post-Meeting Edition), vol. 22, No. 14S (Jul. 15 Suppl.), 2004:2505.

Cancer Therapy Evaluation Program, Common Terminology Criteria for Adverse Events (CTCAE), Version 3.0, DCTD, NCI, NIH, DHHS, Mar. 31, 2003.

Céspedes MV, et al., "Mouse models in oncogenesis and cancer therapy," Clin Transl Oncol. May 2006;8(5):318-29.

Chambers, et al. "Lymphoproliferation in CTLA-4-deficient mice is mediated by costimulation-dependent activation of CD4+ T cells." Immunity. Dec. 1997 vol. 7 (6):885-95.

Chambers, et al. ."Co-stimulation in T cell responses." Curr Opinion Immune. Jun. 1997; vol. 9 (3):396-404.

Damle et al., "Alloantigen-specific cytotoxic and suppressor T lymphocytes are derived from phenotypically distinct precursors," *J Immunol.* (1983);131(5):2296-300.

Dennis C, "Cancer: off by a whisker," Nature. Aug. 17, 2006;442(7104):739-41.

Downey SG, et al., "Prognostic factors related to clinical response in patients with metastatic melanoma treated by CTL-associated antigen-4 blockade," Clin Cancer Res. Nov. 15, 2007;13(22 Pt 1):6681-8. Epub Nov. 2, 2007.

Fujimori K, et al., "A modeling analysis of monoclonal antibody percolation through tumors: a binding-site barrier," J Nucl Med. Jul. 1990;31(7):1191-8.

Gura T, "Systems for identifying new drugs are often faulty," Science. Nov. 7, 1997;278(5340):1041-2.

Hadi et al., "Immunologic and clinical effects of antibody blockade of cytotoxic T lymphocyte-associated antigen 4 in previously vaccinated cancer patients," *PNAS* (2008);105(8):3005-3010.

Hurwitz et al., "Combination immunotherapy of primary prostate cancer in a transgenic mouse model using CTLA-4 blockade," *Cancer Res.* (2000);60(9):2444-8.

Hurwitz et al., "CTLA-4 blockade synergizes with tumor-derived granulocyte-macrophage colony-stimulating factor for treatment of an experimental mammary carcinoma," *Proc. Natl. Acad. Sci. USA* (1998);95:10067-10071.

International Search Report for PCT/US2004/016995, mailed May 10, 2005.

(56) References Cited

OTHER PUBLICATIONS

Jaberipour M, et al., "Increased CTLA-4 and FOXP3 Transcripts in Peripheral Blood Mononuclear Cells of Patients with Breast Cancer," Pathol Oncol Res. Mar. 21, 2010. [Epub ahead of print].
Jain RK, "Barriers to drug delivery in solid tumors," Sci Am. Jul. 1994;271(1):58-65.
Janik et al., "A pilot study of MDX-010 after vaccine failure in patients with advanced malignancy," Blood (2003);102(11):647A, Abstract No. 2391.
Jeffrey A. Bluestone, "Is CTLA-4 a master switch for peripheral T cell tolerance?" J Immune. Mar. 1, 1997;158(5):1989-93.
Kearny, et al. "Antigen-dependent clonal expansion of a trace population of antigen-specific CD4+ T cells in vivo is dependent on CD28 costimulation and inhibited by CTLA-4." J Immunol. Aug. 1, 1995;155(3):1032-6.
Krummel, et al. "CD28 and CTLA-4 Have Opposing Effects on the Response of T cells to Stimulation." J.Exp.Med. vol. 182, pp. 459-465, Aug. 1995.
Krummel, et al. "Superantigen responses and co-stimulation: CD28 and CTLA-4 have opposing effects on T cell expansion in vitro and in vivo" International Immunology, Oct. 1995; vol. 8, No. 4. pp. 519-523.
Langer LF, et al., "Update on anti-CTLA-4 antibodies in clinical trials," Expert Opin Biol Ther. Aug. 2007;7(8):1245-56.
Leach et al., "Enhancement of antitumor immunity by CTLA-4 blockade," Science. (1996);271(5256):1734-6.
Lindsten et al., "Regulation of lymphokine messenger RNA stability by a surface-mediated cell activation pathway," Science. (1989);244(4902):339-43.
Lühder, et al. "Cytotoxic T lymphocyte-associated antigen 4 (CTLA-4) regulates the unfolding of autoimmune diabetes." J Exp Med. Feb. 2, 1998; vol. 187(3):427-32.
Maker AV, et al., "Intrapatient dose escalation of anti-CTLA-4 antibody in patients with metastatic melanoma," J Immunother. Jul.-Aug. 2006;29(4):455-63.
Matsui et al., "Autoantibodies to T cell costimulatory molecules in systemic autoimmune diseases," J Immunol. (1999);162(7):4328-35.
Mokyr et al., "Realization of the therapeutic potential of CTLA-4 blockade in low-dose chemotherapy-treated tumor-bearing mice," Cancer Research (1998);58:5301-5304.
Murata, et al. "Expression of the costimulatory molecule BB-1, the ligands CTLA-4 and CD28, and their mRNA in inflammatory myopathies." Am Jr Pathol. Aug. 1999; vol. 155 (2):453-60.
O'Mahony et al., "A pilot study of CTLA-4 blockade after cancer vaccine failure in patients with advanced malignancy," Clin Cancer Res. (2007);13(3):958-964.
Overwijk et al., "Vaccination with a recombinant vaccinia virus encoding a "self" antigen induces autoimmune vitiligo and tumor cell destruction in mice: requirement for CD4(+) T lymphocytes," Proc Nad Acad Sci U S A. (1999);96(6):2982-7.
Perrin et al., "CTLA-4 blockade enhances clinical disease and cytokine production during experimental allergic encephalomyelitis," J Immunol. (1996);157(4):1333-6.
Phan et al., "Cancer regression and autoimmunity induced by cytotoxic T lymphocyte-associated antigen 4 blockade in patients with metastatic melanoma," Proc Natl Acad Sci U S A. (2003);100(14):8372-7.
Rosenberg and White, "Vitiligo in patients with melanoma: normal tissue antigens can be targets for cancer immunotherapy," J Immunother Emphasis Tumor Immunol. (1996);19(1):81-4.
Rudnick SI, et al., "Affinity and avidity in antibody-based tumor targeting," Cancer Biother Radiopharm. Apr. 2009;24(2):155-61.
Saenger YM, et al., "The heterogeneity of the kinetics of response to ipilimumab in metastatic melanoma: patient cases," Cancer Immun. Jan. 17, 2008;8:1.
Sanderson et al., "Autoimmunity in a phase I trial of a fully human anti-cytotoxic T-lymphocyte antigen-4 monoclonal antibody with multiple melanoma peptides and Montanide ISA 51 for patients with resected stages III and IV melanoma," J Clin Oncol. (2005);23(4):741-50.

Shah KV, et al., "CTLA-4 is a direct target of Wnt/beta-catenin signaling and is expressed in human melanoma tumors," J Invest Dermatol. Dec. 2008;128(12):2870-9. Epub Jun. 19, 2008.
Small et al., "A pilot trial of CTLA-4 blockade with human anti-CTLA-4 in patients with hormone-refractory prostate cancer," Clin. Cancer Res. (2007);13(6):1810-1815.
Tarhini & Kirkwood, "Tremelimumab (CP-675,206) a fully human anticytotoxic T lymphocyte-associated antigen 4 monoclonal antibody for treatment of patients with advanced cancers," Expert Opin. Boil. Ther. (2008); 8(10):1583-1593.
Tassev & Cheung, "Monoclonal antibody therapies for solid tumors," Expert. Opin. Biol. Ther. (2009);9(3):341-353.
Thompson et al., "CD28 activation pathway regulates the production of multiple T-cell-derived lymphokines/cytokines," Proc Natl Acad Sci U S A. (1989);86(4):1333-7.
Thompson, et al. "The emerging role of CTLA-4 as an immune attenuator." Immunity. Oct. 1997;vol. 7 (4):445-50.
Thurber GM, et al., "Antibody tumor penetration: transport opposed by systemic and antigen-mediated clearance," Adv Drug Deily Rev. Sep. 2008;60(12):1421-34. Epub Apr. 24, 2008.
Underhill et al., "Phase I dose escalation trial of tremelimumab (CP-675,206) administered in combination with PF-3512676 in patients with melanoma or other advanced cancers," J Clin. Oncol. (2009);27:15s (Suppl; abstract 3046).
Van Elsas et al., "Elucidating the autoimmune and antitumor effector mechanisms of a treatment based on cytotoxic T lymphocyte antigen-4 blockade in combination with a B16 melanoma vaccine: comparison of prophylaxis and therapy," J Exp Med. (2001);194(4):4819.
Van Elsas et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," J Exp Med. (1999);190(3):355-66.
Voskoglou-Nomikos T, et al., "Clinical predictive value of the in vitro cell line, human xenograft, and mouse allograft preclinical cancer models," Clin Cancer Res. Sep. 15, 2003;9(11):4227-39.
Walunas, et al. "CTLA-4 Can Function as a Negative Regulator of T Cell Activation." Immunity, vol. 1, pp. 405-413, Aug. 1994.
Weber JS. "Tumor evasion may occur via expression of regulatory molecules: a case for CTLA-4 in melanoma," J Invest Dermatol. Dec. 2008;128(12):2750-2.
Weber J, "Review: anti-CTLA-4 antibody ipilimumab: case studies of clinical response and immune-related adverse events," Oncologist. Jul. 2007;12(7):864-72.
Yang et al., "Ipilimumab (anti-CTLA4 antibody) cause regression of metastatic renal cell cancer associated with enteritis and hypophysitis," J. Immunother. (2007);30(8):825-830.
Anderson, DE, et al., "Paradoxical inhibition of T-cell function in response to CTLA-4 blockade; heterogeneity within the human T-cell population," Nature Medicine (2000), vol. 6, pp. 211-214.
Bailint et al., "Antibody Engineering by Parsimonious Mutagenesis," Gene, 137(1993), 109-118.
Barbas et al., "Recognition of DNA by Synthetic Antibodies," J. Am. Chem. SOC, (1994) 116:2161-2162.
Barbas et al., "Human autoantibody recognition of DNA," Proc. Natl. Acad. Sci. USA (1995) 92:2529-2533.
Beiboer et al., "Guided Selection of a Pan Carcinoma Specific Antibody Reveals Similar Binding Characteristics yet Structural Divergence Between the Original Murine Antibody and its Human Equivalent," J. Mol. Biol. (2000) 296:833-849.
Blair et al., "Cutting edge: CTLA-4 ligation delivers a unique signal to resting human CD4 T cells that inhibits interleukin-2 secretion but allows Bcl-XL induction," The J. of Immunology, 160: 12-15 (1998).
Bluestone J.A., Immunity 2:555-559 (1995).
Boon, T. et al., (1992) Advances in Cancer Res. 58: 177-210.
Brunet et al., "A new member of the immunoglobulin superfamily-CTLA-4", Nature 328:267-270 (1987).
Brunet et al., "A differential molecular biology search for genes preferentially expressed in functional T lymphocytes: The CTLA genes", Immunol. Rev. 103: 21-36 (1988).
U.S. Appl. No. 14/263,207, filed Apr. 28, 2014.

(56) References Cited

OTHER PUBLICATIONS

Chambers, CA, et al., "Thymocyte development is normal in CTLA-4-deficient mice," Proceedings of the National Academy of Sciences USA (1997), vol. 94, pp. 9296-9301.
Chang and Siegel "Genetic and immunological properties of phage-displayed human anti-Rh(D) antibodies: implications for Rh(D) epitope topology," *Am. Soc. Hematol* (1998) 21(8): 3066-3078.
Chen et al., "Costimulation of Antitumor Immunity by the B7 Counterreceptor for the T Lymphocyte Molecules CD28 and CTLA-4," Cell 71:1093-1102 (1992).
Chen, J. et al., "Immunoglobulin gene rearrangement in b cell deficient mice generated by targeted deletion of th Jh locus," International Immunology, vol. 5, No. 6, 647-565.
Choi, T. et al., "Transgenic mice containing a human heavy chain immunoglobulin gene fragment cloned in a yeast artificial chromosome," Nature Genetics, vol. 4, pp. 117-123, Jun. 1993.
Clark et al., "Polypeptides on human B lymphocytes associated with cell activation", Human Immunol. 16:100-113 (1986).
Damle et al., "Costimulation of T Lymphocytes with Integrin Ligands Intercellular Adhesion Molecule-1 or Vascular Cell Adhesion Molecule-I Induces Functional Expression of CTLA-4, A Second Receptor for B7," Journal of Immunology 152:2686-2697 (1994).
Damle et al., "Monoclonal antibody analysis of human T lymphocyte subpopulations exhibiting autologous mixed lymphocyte reaction", Proc. Natl. Acad. Sci. 78(8):5096-5098 (1981).
Dariavach et al., "Human Ig superfamily CTLA-4 gene : chromosomal localization and identity of protein sequence between murine and human CTLA-4 cytoplasmic domains", Eur. J. Immunol. 18:1901-1905 (1988).
Ditzel et al., "Determinants of Polyreactivity in a Large Panel of Recombinant Human Antibodies from HIV-1 Infection," *The Journal of Immunology* (1996) 157:739-749.
Egen et al., "CTLA-4: New Insights Into Its Biological Function and Use in Tumor Immunotherapy", Nature Immunology, vol. 3, No. 7, pp. 611-618, Jul. 2002.
Fishwild et al., "High-avidity human lgGk monoclonal antibodies from a novel strain of minilocus mice," Nature Biotechnology 14:845-851 (1996).
Frankel, Arther E., "Increased Sophistication of Immunotixins; Clinical Cancer Research", vol. 8, 942-944, Apr. 2002.
Freeman et al., "B7, A B cell-restricted antigen that identifies preactivated B cells", J. Immunol. 139(10):3260-3267 (1987).
Freeman et al., "B7, A new member of the Ig superfamily with unique expression on activated and neoplastic B cells", J. Immunol. 143(8):2714-2722 (1989).
Freeman, G.J. et al., J. Immunol. 149(12): 3795-3801 (1992).
Freeman et al., "Uncovering of Functional Alternative CTLA-4 Counter-Receptor in B7-Deficient Mice," Science 262:907-909 (1993).
Green, L. et al, "Antigen-specific human monoclonal antibodies from mice engineered with human ig heavy and light chain YACs," Nature Genetics, vol. 7, pp. 13-21, May 1994.
Green, L. et al., "Regulation of B Cell Development by Variable Gene Complexity in Mice Reconstituted with Human Immunoglobulin Yeast Artificial Chromosome," J. Exp. Med., vol. 188, No. 3, 483-495, Aug. 3, 1998.
Gribben, G, et al., Alloantigen and concomitant CTLA4 signaling induces clonal deletion of alloreactive T cells, Blood (1994), vol. 84, pp. 397a (meeting abstract).
Gribben et al., "CTLA4 mediates antigen-specific apoptosis of human T cells," Proc. Natl. Acad. Sci. USA 92: 811-815 (1995).
Honjo and Matsuda, "Immunoglobulin heavy chain loci of mouse and human," *Immunoglobulin Genes*, Second Ed., (1995) edited by to Hanjo and F.W. Alt, Academic Press, Chapter 7.
Harding et al., "CD28-Mediated Signalling Co-Stimulates Murine T Cells and Prevents Induction of Anergy in T-Cell Clones," Nature 356:607-609 (1992).

Heslop, HE, "Cytokine gene transfer in the therapy of malignancy," Baillieres Clinical Haematology (1994), vol. 7, pp. 135-51 (abstract only), Medline 8038497.
Ishida et al., "Production of a diverse repertoire of human antibodies in genetically engineered mice," *Microbiol. Immunol.* (1998) 42(3):143-50.
Jenkins, M.K., "The Ups and Downs of T Cell Costimulation," Immunity 1:443-446 (1994).
Jun. et al., "The B7 and CD28 Receptor Families," Immunology Today, 15(7):321-331 (1994).
Klimka et al., "Human anti-CD30 recombinant antibodies by guided phage antibody selection using cell palming," *British Journal of Cancer* (2000) 83(2):252-260.
Kohno et al., "CD28 molecule as a receptor-like function for accesory signals in cell-mediated augmentation of IL-2 production", Cell. Immunol. vol. 131 (10 pages) (1990).
Krummel et al., "CTLA-4 engagement inhibits IL-2 accumulation activation of resting T-cells," J. Exp. Med 183:2533-2540 (1996).
Kwon et al., "Manipulation of T Cell costimulatory and inhibitory signals for immunotherapy of prostate cancer," Proc. Natl. Acad. Sci. USA 94:8099-8103 (1997).
Lafage-Poclaitaloff et al., "Human CD28 and CTLA-4 Ig superfamily genes are located on chromosome 2 at bands q33-q34",Immunogenetics 31:198-201 (1990).
Lee, et al., "Increased vaccine-specific T cell frequency after peptide-based vaccination correlates with increased susceptibility to in vitro stimulation but does not lead to tumor regression," Journal of Immunology (1999), vol. 163, pp. 6292-6300.
Lenschow et al., "Long-Term Survival of Xenogeneic Pancreatic Islet Grafts Induced by CTLA4Ig," Science 257:789-792 (1992).
Lenschow et al., "Expression and Functional Significance of an Additional Ligand for CTLA-4," Proc. Natl. Acad. Sci, USA 90:11054-11058 (1993).
Lesslauer et al., "T90/44 (9.3 antigen) A cell surface molecule with a function in human T cell activation", Eur. J. Immunol. 16:1289-1296 (1986).
Lin et al., "Long-Teitti Acceptance of Major Histocompatibility Complex Mismatched Cardiac Allografts Induced by CTLA4Ig Plus Donor-Specific Transfusion," J. Exp. Med. 178:1801-1806 (1993).
Lindsten et al., "Characterization of CTLA-4 Structure and Expression on Human T Cells"; The Journal of Immunology, vol. 151, 3489-3499, No. 7, Oct. 1, 1993.
Linsley et al., "Coexpressiona nd functional cooperation of CTLA-4 and CD28 on activated T lymphocytes" J. Exp. Med. 176:1595-1604 (1992).
Linsley et al. "CTLA-4 is a second receptor for the B cell activation antigen B7," J. Exp. Med. 174:561-569 (1991).
Linsley et al., "Binding of the B cell activation antigen B7 and CD28 costimulates T cell proliferation and interleukin 2 mRNA accumulation", J. Exp. Med. 173:721-730 (1991).
Linsley et al., "T-cell antigen CD28 mediates adhesion with B cells by interacting with activation antigen B7/BB-1", Proc. Natl. Acad. Sci. USA 87:5031-5035 (1990).
Linsley, P.S., "Distinct roles for CD28 and Cytotoxic T Lymphocyte-associated molecule-4 Receptors during T Cell Activation?", J. Exp. Med., The Rockefeller University Press, vol. 182, 289-292, Aug. 1995.
Linsley et al., "Immunosuppression in Vivo by a Soluble Form of the CTLA-4 T Cell Activation Molecule," Science 257:792-795 (1992).
Linsley, P.S., et al., J. Immunol. 150: 3161-3169 (1993).
Linsley, P.S. and J.A. Ledbetter, "The Role of the CD28 Receptor During T Cell Responses to Antigen," Ann. Rev. Immunol. 11:191-212 (1993).
Lonberg, N. et al, "Antigen-specific human antibodies from mice comprising four distinct genetic modifications," Nature, vol. 368:856-859, Apr. 28, 1994.
Longberg et al., "Human antibodies from transgenic mice," International Review of Immunology 13:65-93 (1995).
McCoy et al., "Protective immunity to nematode infection is induced by CTLA-4 blockade," J. Exp. Med 186:183-187 (1997).
Mendez, M. et al., "Functional transplant of megabase human immunoglobulin loci recapitulates human antibody response in mice," Nature Genetics, vol. 15:146-156, Feb. 1997.

(56) References Cited

OTHER PUBLICATIONS

Mukherji, B. et al., (1995) Proc. Natl. Acad. Sci. USA. 92: 8078-8092.
Neuberger, "Generating high-avidity human Mabs in mice," Nature Biotechnology 14:826 (1996).
Panka et al., 1988, Proc. Natl. Acad. Sci. USA, 85: 3080-3084.
Rader et al., "A phage display approach for rapid antibody humanization: Designed combinatorial V gene libraries," Proc. Natl. Acad. Sci. USA (1998) 95:8910-8915.
Rudikoff et al., 1982, Proc. Natl. Acad. Sci. USA, 79: 1979-1983.
Schäble and Zachau "The variable genes of the human immunoglobulin κ locus" Biol. Chem. (1993) 374(11):1001-1022.
Schwartz, R.H., "Costimulation of T Lymphocytes: The Role of CD28, CTLA-4, and B7/BB1 in Interleukin-2 Production and Immunotherapy," Cell 71:1065-1068 (1992).
Shaw et al., "Adjuvant immunotherapy for patients with melanoma: are patients with melanoma of the head and neck candidates for this therapy?" Head and Neck (1997) 19:595-603.
Sotomayor, EM, et al., "In vivo blockade of CTLA-4 enhances the priming of responsive T cells but fails to prevent the induction of tumor antigen-specific tolerance," Proceedings of the National Academy of Science USA (1999), vol. 96, pp. 11476-11481.
Sullivan, T.J. et al., "Induction of CNS inflammatory disease as a consequence of CTLA-4/B7 blockade," FASEB Journal (1998), vol. 12, pp. A1092 (meeting abstract).
Taylor, L. et al., "A transgenic mouse that expresses a diversity of human sequence heavy and light chain immunoglobulins," Nucleic Acids Research, 1992, vol. 20, No. 23, 6287-6295.
Taylor, L. et al., "Human immunoglobulin transgenes undergo rearrangement, somatic class switching in mice that lack endogenous IgM," International Immunology, vol. 6, No. 4, 579-591.
Timmerman, J.M. et al., "Dendritic cell vaccines for cancer immunotherapy," Annual Review of Medicine (1999), vol. 50, pp. 507-529.
Townsend, S.E. and J.P. Allison, "Tumor Rejection After Direct Costimulation of CD8+ T Cells by B7-Transfected Melanoma Cells," Science 259:368-370 (1993).
Tuaillon, N. et al., "Analysis of Direct and Inverted DJh Rearrangements in a Human Ig Heavy Chain Transgenic Minilocus," The Journal of Immunology, vol. 154: 6453-6465, 1995.
Tuaillon, N. et al., "Human immunoglobulin heavy-chain minilocus recombination in transgenic mice: Gene-segment use in μ and y transcripts," Proc. Natl. Acad. Sci. USA., vol. 99: 3720-3724, Apr. 1993, Immunology.
Turka et al., "T-Cell Activation by the CD28 Ligand B7 is Required for Cardiac Allograft Rejection in vivo," Proc. Natl. Acad. Sci. USA 89:11102-11105 (1992).
Walunas et al., "CTLA-4 ligation blocks CD28-dependent T cell activation," J. Exp. Med 183:2541-2550 (1996).
Wen Y.J. et al., (1998) Clin. Cancer Res. 4: 957-962.
Wu et al., "CTLA-4-B7 Interaction is Sufficient to Costimulate T Cell Clonal Expansion," J. Exp. Med. 185(7):1327-1335 (1997).
Yang, Y-F, et al., "Enhanced induction of antitumor T-cell responses by cytotoxic lymphocyte-associated molecule-4 blockade: the effect is manifested only at the restricted tumor-bearing stages," Cancer Research (1997), vol. 57, pp. 4036-4041.
Yang et al., "Eradication of established tumors by a fully human monoclonal antibody to the epidermal growth factor receptor without concomitant chemotherapy," Cancer Research 59:1236-1243 (1999).
Yanofsky, S.D. et al., "High affinity type I interleukin receptor antagonists discovered by screening recombinant peptide libraries," (1996) Proc. Natl. Acad. Sci. USA 93: 7381-7386.
Yokochi et al., "B lymphobalst antigen (BB-1) expressed on epstein-barr virus-activated B cell blasts, B lymphoblastoid cell lines, and burkitt's lymphomas", J. Immunol. 128:823-827 (1981).
Zachau, "The human immunoglobulin K genes," Immunoglobulin Genes, Second Ed., (1995) edited by to Hanjo and F.W. Alt, Academic Press, Chapter 8.

Zaks, T.Z. and Rosenberg S.A., "Immunization with a peptide epitope (p369-377) from HER-2/neu leads to peptide-specific cytotoxic T lymphocytes that fail to recognize HER-2/neu+ tumors," Cancer Research (1998), vol. 58, pp. 4902-4908.
Zhu, J. et al., "Cytotoxic T lymphocyte-associated antigen 4 (CTLA-4) blockade enhances incidence and severity of experimental autoimmune neuritis in resistant mice," Journal of Neuroimmunology (2001), 115: 111-117.
Brown et al., "Tumor necrosis factor antagonist therapy and lymphoma development", (2002) Arthritis and Rheumatism, 46(12): 3151-3158.
Chambers, et al., 1999, "Cytotoxic T lymphocyte antigen-4 (CTLA-4) regulates primary and secondary peptide-specific CD3$^+$T cell responses," Proc. Natl. Acad. Sci. USA, vol. 96: p. 8603-8608.
Chambers et al., 1998, "Secondary but not primary T cell responses are enhanced in CTLA-4-deficient CD8$^+$T cells," Eur. J. Immunol., vol. 28: p3137-43.
Chambers et al., "CTLA-4-mediated inhibition in regulation of T cell responses: mechanisms and manipulation in tumor immunotherapy", Annu Rev Immunol. (2001); 19:565-94.
Doyle, et al., 2001, "Induction of cytotoxic T lymphocyte antigen 4 (CTLA-4) restricts clonal expansion of helper T cells," J. Exp. Med., vol. 194: p. 893-902.
European Search Report for EP 03728392.6, dated Apr. 29, 2005.
Falko-Gunter Falkner,—F.3d—, 2006 WL 1453040, 1-15.
Gray et al., "Therapeutic potential of immunostimulatory monoclonal antibodies", Clinical Science, 2006, 111:93-106.
Gulley et al., "Future directions in tumor immunotherapy", Nat Clin Pract Oncol. (2007); 4(3): 136-137.
Hochberg et al., "The benefit/risk profile of TNF-Blocking agents: Findings of a consensus panel", Semin. Arthritis Rheum., 2005, 34:819-836.
Hodi et al., 2003, "Biologic activity of cytotoxic T lymphocyte-associated antigen 4 antibody blockade in previously vaccinated metastatic melanoma and ovarian carcinoma patients," Proc. Natl. Acad. Sci. USA, vol. 100: p. 4712-17.
Hodi and Dranoff, 2006, "Combinatorial cancer immunotherapy," Adv. Immunol., vol. 90: p. 341-68.
Huang, Z., "Structural chemistry and therapeutic intervention of protein-protein interactions in immune response, human immunodeficiency virus entry, and apoptosis", Pharmacology and Therapeutics, 2000, 86: 201-215.
Jago et al., 2004, "Differential expression of CTLA-4 among T cell subsets," Clin. Exp. Immunol., vol. 136: p. 463-71.
Keler et al., 2003, "Activity and safety of CTLA-4 blockade combined with vaccines in Cynomolgus Macaques," J. Immunol., vol. 171: p. 6251-59.
Macon-Lemaitre and Triebel, 2005, "The negative regulatory function of the lymphocyte-activation gene-3 co-receptor (CD223) on human T cells," Immunology, vol. 115: p. 170-178.
Metz, et al., 1998, "Differential role of CTLA-4 in regulation of resting memory versus naive CD4 T cell activation," J. Immunol., vol. 161: p. 5855-61.
Ribas et al., 2005, "Role of dendritic cell phenotype, determinant spreading, and negative costimulatory blockade in dendritic cell-based melanoma immunotherapy," J. Immunother., vol. 27: p. 354-67.
Rosenberg, "A new era for cancer immunotherapy based on the genes that encode cancer antigens," Immunity, 1999; 10:281-7.
Saenger et al., Can. Immun. 8: 1-7 (Jan. 2008).
Spencer et al., "Distinct inflammatory mechanisms mediate early versus late colitis in mice", Gastroenterology, 2002, 122:94-109.
Titelbaum et al., "anti-tumor necrosis factor alpha-associated multiple sclerosis", AJNR Am J Neuroradiol, 26: 1548-1550, Jun./Jul. 2005.
Tivol, et al., "Loss of CTLA-4 leads to massive lymphoproliferation and fatal multiorgan tissue destruction, revealing a critical negative regulatory role of CTLA-4", Immunity, 3(5):541-547 (1995).
Van Assche et al., Curr. Opin. Gastroenterol., Jul. 2005, 21: 443-447.
Zenapax® package insert and information, 2005.

* cited by examiner

SEQUENCE LISTING

```
<160> NUMBER OF SEQ ID NOS: 8

<210> SEQ ID NO 1
<211> LENGTH: 5
<212> TYPE: PRT
<213> ORGANISM: Homo sapiens
<220> FEATURE:
<223> OTHER INFORMATION: heavy chain CDR1 for MDX-010

<400> SEQUENCE: 1

Ser Tyr Thr Met His
1               5

<210> SEQ ID NO 2
<211> LENGTH: 17
<212> TYPE: PRT
<213> ORGANISM: Homo sapiens
<220> FEATURE:
<223> OTHER INFORMATION: heavy chain CDR2 for MDX-010

<400> SEQUENCE: 2

Phe Ile Ser Tyr Asp Gly Asn Asn Lys Tyr Tyr Ala Asp Ser Val Lys
1               5                   10                  15

Gly

<210> SEQ ID NO 3
<211> LENGTH: 9
<212> TYPE: PRT
<213> ORGANISM: Homo sapiens
<220> FEATURE:
<223> OTHER INFORMATION: heavy chain CDR3 for MDX-010
```

```
<400> SEQUENCE: 3

Thr Gly Trp Leu Gly Pro Phe Asp Tyr
 1               5

<210> SEQ ID NO 4
<211> LENGTH: 12
<212> TYPE: PRT
<213> ORGANISM: Homo sapiens
<220> FEATURE:
<223> OTHER INFORMATION: light chain CDR1 for MDX-010

<400> SEQUENCE: 4

Arg Ala Ser Gln Ser Val Gly Ser Ser Tyr Leu Ala
 1               5                  10

<210> SEQ ID NO 5
<211> LENGTH: 7
<212> TYPE: PRT
<213> ORGANISM: Homo sapiens
<220> FEATURE:
<223> OTHER INFORMATION: light chain CDR2 for MDX-010

<400> SEQUENCE: 5

Gly Ala Phe Ser Arg Ala Thr
 1               5

<210> SEQ ID NO 6
<211> LENGTH: 9
<212> TYPE: PRT
<213> ORGANISM: Homo sapiens
<220> FEATURE:
<223> OTHER INFORMATION: light chain CDR3 for MDX-010

<400> SEQUENCE: 6

Gln Gln Tyr Gly Ser Ser Pro Trp Thr
 1               5

<210> SEQ ID NO 7
<211> LENGTH: 118
<212> TYPE: PRT
<213> ORGANISM: Homo sapiens
<220> FEATURE:
<223> OTHER INFORMATION: heavy chain variable region sequence for
      MDX-010

<400> SEQUENCE: 7

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115
```

```
<210> SEQ ID NO 8
<211> LENGTH: 108
<212> TYPE: PRT
<213> ORGANISM: Homo sapiens
<220> FEATURE:
<223> OTHER INFORMATION: light chain variable region sequence for
      MDX-010

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
                100                 105
```

CTLA-4 ANTIBODY DOSAGE ESCALATION REGIMENS

CROSS-REFERENCE TO RELATED APPLICATIONS

This application is a continuation application of U.S. application Ser. No. 11/567,846, filed Dec. 7, 2006, issued as U.S. Pat. No. 8,110,194, which claims priority to U.S. Provisional application Ser. No. 60/748,688, filed on Dec. 7, 2005, all of which are incorporated herein by reference in their entirety.

SEQUENCE LISTING

The specification further incorporates by reference the Sequence Listing submitted herewith via EFS on Oct. 16, 2014. Pursuant to 37 C.F.R. §1.52(e)(5), the Sequence Listing text file, identified as "0773750941SEQLIST.TXT," is 3,638 bytes and was created on Oct. 3, 2014. The Sequence Listing, electronically filed herewith, does not extend beyond the scope of the specification and thus does not contain new matter.

FIELD OF THE INVENTION

The present invention relates to methods of treating a disease, such as cancer or an infectious disease, in a patient by administering a CTLA-4 antibody to the patient in an escalating dosage regimen until an optimum dosage is reached.

BACKGROUND OF THE INVENTION

The vertebrate immune system requires multiple signals to achieve optimal immune activation (see, e.g., Janeway, Cold Spring Harbor Symp. Quant. Biol. 1989; 54:1-14; Paul William E., ed. Raven Press, N.Y., Fundamental Immunology, 4th edition (1998), particularly chapters 12 and 13, pages 411 to 478). Interactions between T lymphocytes (T cells) and antigen presenting cells (APC) are essential to the immune response. Levels of many cohesive molecules found on T cells and APC's increase during an immune response (Springer et al., A. Rev. Immunol. 1987; 5:223-252; Shaw and Shimuzu, Current Opinion in Immunology, 1988 Eds. Kindt and Long, 1:92-97; and Hemler, Immunology Today 1988; 9:109-113). Increased levels of these molecules may help explain why activated APC's are more effective at stimulating antigen-specific T cell proliferation than are resting APC's (Kaiuchi et al., J. Immunol. 1983; 131:109-114; Kreiger et al., J. Immunol. 1985; 135:2937-2945; McKenzie, J. Immunol. 1988; 141:2907-2911; and Hawrylowicz and Unanue, J. Immunol. 1988; 141:4083-4088).

T cell immune response is a complex process that involves cell-cell interactions (Springer et al., A. Rev. Immunol. 1987; 5:223-252), particularly between T and accessory cells such as APC's, and production of soluble immune mediators (cytokines or lymphokines) (Dinarello, New Engl. J. Med 1987; 317:940-945; Sallusto, J. Exp. Med. 1997; 179:1109-1118). This response is regulated by several T-cell surface receptors, including the T-cell receptor complex (Weiss, Ann. Rev. Immunol. 1986; 4:593-619) and other "accessory" surface molecules (Allison, Curr. Opin. Immunol. 1994; 6:414-419; Springer, 1987, supra). Many of these accessory molecules are naturally occurring cell surface differentiation (CD) antigens defined by the reactivity of monoclonal antibodies on the surface of cells (McMichael, Ed., *Leukocyte Typing III*, Oxford Univ. Press, Oxford, N.Y., 1987).

CD28 antigen, a homodimeric glycoprotein of the immunoglobulin superfamily (Aruffo and Seed, Proc. Natl. Acad. Sci. 1987; 84:8573-8577), is an accessory molecule found on most mature human T cells (Damle et al., J. Immunol. 1983; 131:2296-2300). Current evidence suggests that this molecule functions in an alternative T cell activation pathway distinct from that initiated by the T-cell receptor complex (June et al., Mol. Cell. Biol. 1987; 7:4472-4481). Monoclonal antibodies (MAbs) reactive with CD28 antigen can augment T cell responses initiated by various polyclonal stimuli (reviewed by June et al., supra). These stimulatory effects may result from MAb-induced cytokine production (Thompson et al., Proc. Natl. Acad. Sci 1989; 86:1333-1337; and Lindsten et al., Science 1989; 244:339-343) as a consequence of increased mRNA stabilization (Lindsten et al., 1989, supra).

CTLA-4 (cytotoxic T lymphocyte-associated antigen-4) is accepted as opposing CD28 activity and dampening T cell activation (Krummel, J. Exp. Med. 1995; 182:459-465; Krummel et al., Int'l Immunol. 1996; 8:519-523; Chambers et al., Immunity. 1997; 7:885-895). CTLA-4 deficient mice suffer from massive lymphoproliferation (Chambers et al., supra). It has been reported that CTLA-4 blockade augments T cell responses in vitro (Walunas et al., Immunity. 1994; 1:405-413) and in vivo (Kearney, J. Immunol. 1995; 155: 1032-1036), exacerbates antitumor immunity (Leach, Science 1996; 271:1734-1736), and enhances an induced autoimmune disease (Luhder, J Exp. Med. 1998; 187:427-432). It has also been reported that CTLA-4 has an alternative or additional impact on the initial character of the T cell immune response (Chambers, Curr. Opin. Immunol. 1997; 9:396-404; Bluestone, J. Immunol. 1997; 158:1989-1993; Thompson, Immunity 1997; 7:445-450). This is consistent with the observation that some autoimmune patients have autoantibodies to CTLA-4. It is possible that CTLA-4 blocking autoantibodies play a pathogenic role in these patients (Matsui, J. Immunol. 1999; 162:4328-4335).

Non-human CTLA-4 antibodies have been used in the various studies discussed above. Furthermore, human antibodies against human CTLA-4 have been described as immunostimulation modulators in a number of disease conditions, such as treating or preventing viral and bacterial infection and for treating cancer (e.g., PCT Publication WO 01/14424 and PCT Publication WO 00/37504). U.S. Pat. No. 5,855,887 discloses a method of increasing the response of a mammalian T cell to antigenic stimulation by combining a T cell with a CTLA-4 blocking agent. U.S. Pat. No. 5,811,097 discloses a method of decreasing the growth of non-T cell tumors by administering a CTLA-4 blocking agent. U.S. Pat. No. 6,984, 720 and U.S. Patent Publication No. 2002/0086014 disclose human CTLA-4 antibodies. Each of these patents and applications is hereby incorporated by reference.

U.S. Patent Publication No. 2004/0241169 describes a treatment for cancer in which the target dosage of a CTLA-4 antibody for a patient is a dosage that results in an autoimmune event.

There continues to be a need for methods of administering an optimum dose of a CTLA-4 antibody for the treatment of a disease, such as cancer or infectious disease, to a patient that meets a predetermined maximum dosage level, or results in a partial or complete response, and minimizes the incidence and/or severity of an adverse event.

SUMMARY OF THE INVENTION

This invention is directed to methods of administering a CTLA-4 antibody to a patient in a dosage escalation regimen for treating a disease or condition, such as cancer or an infectious disease, by administering escalating dosages of the CTLA-4 antibody to the patient until an optimum dosage is reached.

The present invention provides methods for treating cancer in a patient by administering a CTLA-4 antibody to the patient according to a dosage escalation regimen, which comprises administering increasing dosages of the CTLA-4 antibody to the patient until an optimum dosage is reached.

In one embodiment, the escalating dosage regimen includes a linear increase in CTLA-4 antibody dosage. In another embodiment, the escalating dosage regimen includes a stepwise increase in CTLA-4 antibody dosage.

According to the present invention, a dosage escalation regimen permits a patient to receive an optimum dosage of a CTLA-4 antibody, which is a dosage that results in a partial or complete response in the patient, or is a predetermined maximum dosage.

In an embodiment of the invention, a dosage of CTLA-4 antibody is administered about every three weeks.

In a specific embodiment, the escalating dosage regimen includes administering a first dosage of CTLA-4 antibody at about 3 mg/kg, a second dosage of CTLA-4 antibody at about 5 mg/kg, and a third dosage of CTLA-4 antibody at about 9 mg/kg.

In another specific embodiment, the escalating dosage regimen includes administering a first dosage of CTLA-4 antibody at about 5 mg/kg and a second dosage of CTLA-4 antibody at about 9 mg/kg.

Further, the present invention provides an escalating dosage regimen, which includes administering an increasing dosage of CTLA-4 antibody about every six weeks.

In an aspect of the present invention, a stepwise escalating dosage regimen is provided, which includes administering a first CTLA-4 antibody dosage of about 3 mg/kg, a second CTLA-4 antibody dosage of about 3 mg/kg, a third CTLA-4 antibody dosage of about 5 mg/kg, a fourth CTLA-4 antibody dosage of about 5 mg/kg, and a fifth CTLA-4 antibody dosage of about 9 mg/kg. In another aspect of the present invention, a stepwise escalating dosage regimen is provided, which includes administering a first dosage of 5 mg/kg, a second dosage of 5 mg/kg, and a third dosage of 9 mg/kg.

The present invention further provides methods for treating infectious disease in a patient comprising administering a CTLA-4 antibody to the patient according to a dosage escalation regimen, which includes administering increasing dosages of the CTLA-4 antibody to the patient until an optimum dosage is reached.

In particular embodiments of the present invention, the CTLA-4 antibody is a human sequence antibody. In a more particular embodiment, the CTLA-4 antibody is MDX-010, also referred to as ipilimumab. The MDX-010 antibody comprises a heavy chain variable region that comprises CDR1, CDR2, and CDR3 domains; and a light chain variable region that comprises CDR1, CDR2, and CDR3 domains, wherein the heavy chain variable region CDR1 comprises amino acids having the sequence set forth in SEQ ID NO:1; the heavy chain variable region CDR2 comprises amino acids having the sequence set forth in SEQ ID NO:2; the heavy chain variable region CDR3 comprises amino acids having the sequence set forth in SEQ ID NO:3; the light chain variable region CDR1 comprises amino acids having the sequence set forth in SEQ ID NO:4; the light chain variable region CDR2 comprises amino acids having the sequence set forth in SEQ ID NO:5; and the light chain variable region CDR3 comprises amino acids having the sequence set forth in SEQ ID NO:6. The MDX-010 antibody comprises a heavy chain variable region comprising amino acids comprising the sequence set forth in SEQ ID NO:7. The MDX-010 antibody comprises a light chain variable region comprising amino acids comprising the sequence set forth in SEQ ID NO:8.

In embodiments of the present invention, a CTLA-4 antibody can be administered according to a dosage escalation regimen in combination with a vaccine (e.g., gp100, tyrosinase or MART-1), a chemotherapeutic agent (e.g., cyclophosphamide or dacarbazine), or a cytokine (e.g., IL-2).

DETAILED DESCRIPTION OF THE INVENTION

It has been surprisingly found that a patient receiving a CTLA-4 antibody in an escalating dosage regimen according to the present invention can tolerate an optimum dose of the antibody. The methods of the present invention include dosage escalation regimens that permit a patient to tolerate a dosage of a CTLA-4 antibody that is about three times greater than previously reported maximum dosages. For example, the present invention provides a method for administering a 9 mg/kg dose of a CTLA-4 antibody to a patient, and previous studies reported a maximum CTLA-4 antibody dose of 3 mg/kg (see, e.g., the clinical studies disclosed in U.S. Patent Publication No. 2004/0241169).

The methods of the present invention are based, in part, on the clinical study summarized below and described further in the example.

In a clinical study, 46 HLA-A2 negative patients with progressive stage IV melanoma were treated with a CTLA-4 antibody according to a dose escalation regimen. Twenty-three patients started CTLA-4 antibody therapy at 3 mg/kg and 23 patients started therapy at 5 mg/kg. The patients received progressively increased doses of the CTLA-4 antibody until an objective clinical response was observed, a maximum of 9 mg/kg was reached, or a grade III/IV autoimmune toxicity occurred. Five patients (11%) had an objective clinical response. Two of the responses occurred without grade III/IV autoimmune toxicity. One of the responses occurred without autoimmune toxicity. To date, four of the responses are ongoing.

2.1. Escalating Dosage Regimens

The present invention includes methods for escalating the dosage of a CTLA-4 antibody administered to a patient until a partial or complete response is elicited in the patient, or a pre-determined maximum dosage is reached.

As used herein, a "complete response" means a complete disappearance of a symptom or objective indicia of a disease. For example, a complete response in a patient with a tumor means the disappearance of all measurable lesions for greater than or equal to one month. For patients with infectious diseases, a complete response means the complete clearance of the infectious toxin or pathogen from the patient (as measured by, e.g., a body fluid culture) or the complete resolution of all signs and symptoms associated with the infectious disease (e.g., fever, cough, leukocytosis).

As used herein, a "partial response" means a response that is less than a complete response. For example, a partial response in a patient with a tumor is a decrease of approximately greater than or equal to 30% (but not 100%) of the sum of the longest diameters of index (baseline) lesions, lasting at least one month with no growth of lesions or the appearance of new lesions. Tumor size can be measured directly or using an imaging study (e.g., a CT, MRI, or sonogram). For infectious diseases, a partial response, means an improvement, but not complete resolution of, the signs and symptoms associated with the infectious disease or a decrease in the infectious toxin or pathogen in a patient (e.g., a decreased viral load in the case of HIV).

A "pre-determined maximum dosage" or a "pre-determined maximum dose" is a target endpoint dosage that is defined before the administration of the CTLA-4 dosage regimen. For example, prior to administration of the first dose of a CTLA-4 antibody to a patient, a clinician can identify 9 mg/kg of the CTLA-4 antibody as the predetermined maximum dosage.

An "optimal" or "optimum" dose of a CTLA-4 antibody is the dose corresponding to a predetermined maximum dose, or a dose that results in a partial or complete response to the disease being treated. It shall be appreciated by those of skill in the art that factors, including the patient's immune state, which may be affected by prior immune therapies, disease state, age, etc., can impact the dosage required to elicit a complete or partial response, or determine a pre-determined maximum dosage. A skilled clinician will be able to take such factors into account when determining the initial dose, as well as any subsequent doses, to obtain an optimum dosage. Typically, a CTLA-4 antibody dosage is about 0.1 mg/kg to about 25 mg/kg.

An "adverse event" (AE) as used herein is any unfavorable and generally unintended, even undesirable, sign (including an abnormal laboratory finding), symptom, or disease associated with the use of a medical treatment (e.g., CTLA-4 antibody therapy). Most AE's are temporary and reverse upon withdrawal or reduction in dose of the medical treatment, or with treatment of the AE.

A "serious adverse event" (SAE) is a grade III or IV adverse event as defined by the National Cancer Institute (NCI). A grade III AE is generally defined as "severe" and a grade IV AE is generally defined as "life-threatening or disabling".

Adverse events associated with CTLA-4 antibody administration include: skin rash, vitiligo, hypophysitis, colitis, diarrhea, dermatitis, uveitis, nephritis, and increased liver enzymes. See also U.S. Patent Publication No. 2004/0241169 (the contents of which are hereby incorporated by reference in their entirety) for a description of certain adverse events associated with CTLA-4 antibody therapy. An adverse event associated with CTLA-antibody therapy can limit, or cause the cessation of, the CTLA-4 antibody therapy.

As used herein, an "escalating dosage regimen" or "dosage escalation regimen" is a dosage regimen administered to a patient wherein dosages in a series can be increased in a stepwise (i.e., a subsequent dosage is either greater than or equal to the immediately preceding dosage, but at least one increase in dosage occur over the length of the regimen) or linear fashion (i.e., each subsequent dosage is greater than its immediately preceding dosage).

An initial dose of a CTLA-4 antibody is typically about 0.1 mg/kg to about 10 mg/kg, and more typically about 3 mg/kg to about 10 mg/kg. Following an initial dose of CTLA-4 antibody, a patient is monitored by a clinician for a sufficient period of time, which is typically over the course of the dosage interval (e.g., 1 to 8 weeks, preferably 1 to 4 weeks) to detect a partial or complete response. In the absence of a partial or complete response during the monitoring period, a second dose of CTLA-4 antibody can be administered that is greater than or equal to the first dose. Following this second dose, the patient is again monitored for a partial or complete response. Additional dosages greater than or equal to the immediately prior dose are administered in a stepwise or linear fashion until a partial or complete response is elicited, or a pre-determined maximum dosage is obtained. If an additional dose is required, the dosage can be increased by, e.g., about 10% to about 100% of the immediately preceding dosage.

In one example of a linear dosage regimen, a patient is initially administered about 3 mg/kg of a CTLA-4 antibody. If the patient does not achieve a partial or complete response after a 3 week period, then the patient is administered about 5 mg/kg of CTLA-4 antibody.

In one example of a stepwise dosage regimen, a patient is initially administered about 3 mg/kg of a CTLA-4 antibody followed by a second dose of about CTLA-4 antibody at 3 mg/kg. Subsequent doses of CTLA-4 antibody, in order, include about 5 mg/kg, about 5 mg/kg, about 9 mg/kg, and about 9 mg/kg. A dosage according to this example is administered every 3 weeks. The patient is monitored throughout the regimen to determine whether a partial or complete response has been achieved. If the patient does not achieve a partial or complete response before the next scheduled dosage, the next scheduled dosage is administered. If the patient does achieve a partial response, the patient is not given the next scheduled dosage or is administered a dosage approximately equal to the immediately preceding dosage.

2.2. General Definitions

Except when noted, the terms "patient" or "subject" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

The term "treating" includes the administration of CTLA-4 antibodies of the present invention to prevent or delay the onset of the symptoms, complications, or biochemical indicia of a disease, alleviating the symptoms or arresting or inhibiting further development of the disease, condition, or disorder (e.g., cancer, an infectious disease, or an autoimmune disease). Treatment may be prophylactic (to prevent or delay the onset of the disease, or to prevent the manifestation of clinical or subclinical symptoms thereof) or therapeutic suppression or alleviation of symptoms after the manifestation of the disease.

The terms "about" or "approximately" mean within an acceptable range for the particular parameter specified as determined by one of ordinary skill in the art, which will depend in part on how the value is measured or determined, e.g., the limitations of the measurement system. For example, "about" can mean a range of up to 20% of a given value. Alternatively, particularly with respect to biological systems or processes, the term can mean within an order of magnitude, preferably within 5-fold, and more preferably within 2-fold, of a value.

2.3. CTLA-4 Antibodies

The terms "cytotoxic T lymphocyte-associated antigen-4," "CTLA-4," "CTLA4," "CTLA-4 antigen" and "CD152" (see, e.g., Murata (1999) Am. J. Pathol. 155:453-460) are used interchangeably, and include variants, isoforms, species homologs of human CTLA-4, and analogs having at least one common epitope with CTLA-4 (see, e.g., Balzano (1992) Int. J. Cancer Suppl. 7:28-32). A complete sequence of human CTLA-4 is set forth in GenBank Accession No. L15006.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term antibody includes antigen-binding portions of an intact antibody that retain capacity to bind CTLA-4. Examples of binding include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al., Science 1998; 242:423-426; and Huston et al., Proc. Natl. Acad. Sci. USA 1988; 85:5879-5883). Such single chain antibodies are included by reference to the term "antibody." Fragments can be prepared by recombinant techniques or enzymatic or chemical cleavage of intact antibodies.

The term "human sequence antibody" includes antibodies having variable and constant regions (if present) derived from human germline immunoglobulin sequences. The human sequence antibodies of the invention may include amino acid residues not encoded by human germline immunoglobulin sequences (e.g., mutations introduced by random or site-specific mutagenesis in vitro or by somatic mutation in vivo). Such antibodies can be generated in non-human transgenic animals, i.e., as described in PCT Publication Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (i.e., humanized antibodies).

The terms "monoclonal antibody" or "monoclonal antibody composition" refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "polyclonal antibody" refers to a preparation of more than 1 (two or more) different antibodies to human CTLA-4. Such a preparation includes antibodies binding to a range of different epitopes.

CTLA-4 antibodies can bind to an epitope on human CTLA-4 so as to inhibit CTLA-4 from interacting with a human B7 counterreceptor. Because interaction of human CTLA-4 with human B7 transduces a signal leading to inactivation of T-cells bearing the human CTLA-4 receptor, antagonism of the interaction effectively induces, augments or prolongs the activation of T cells bearing the human CTLA-4 receptor, thereby prolonging or augmenting an immune response. CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication No. 2002/0039581 and 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al., PNAS 1998; 95(17):10067-10071; Camacho et al., J Clin Oncology 2004:22(145): abstract no. 2505 (antibody CP-675206); and Mokyr, et al., Cancer Research 1998; 58:5301-5304. Each of these references is specifically incorporated herein by reference for purposes of description of CTLA-4 antibodies. A preferred clinical CTLA-4 antibody is human monoclonal antibody 10D1 (also referred to as MDX-010 and ipilimumab and available from Medarex, Inc., Bloomsbury, N.J.) as disclosed in WO 01/14424.

Also included in the invention are modified antibodies. The term "modified antibody" includes antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody.

Antibody conjugates are also contemplated for use in the methods of this invention and can be used to modify a given biological response or create a biological response (e.g., to recruit effector cells). An "antibody conjugate," as used herein, is a CTLA-4 antibody conjugated to a drug moiety. The drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-alpha; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

2.4. Cancer Treatment

The present invention is directed, in part, to the treatment of tumors, particularly immunologically sensitive tumors, which are cancers that respond to immunotherapy or cancers that manifest in patients who are immunocompromised. A tumor treated with the methods of this invention can be a solid tumor.

Examples of tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, lymphoma, melanoma, Kaposi's sarcoma, Ewing's tumor, leiomyosarcoma, rhabdomyosarcoma, colo-rectal carcinoma, gastric carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The methods of this invention can also treat or prevent dysproliferative changes (such as metaplasias and dysplasias) in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W.B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, *Medicine*, 2d Ed., J. B. Lippincott Co., Philadelphia.

The present invention is also directed to treatment of non-malignant tumors and other disorders involving inappropriate cell or tissue growth augmented by angiogenesis by administering a therapeutically effective amount of a vector of the invention to the tissue undergoing inappropriate growth. For example, it is contemplated that the invention is useful for the treatment of arteriovenous (AV) malformations, particularly in intracranial sites. The invention may also be used to treat psoriasis, a dermatologic condition that is characterized by inflammation and vascular proliferation; and benign prostatic hypertrophy, a condition associated with inflammation and possibly vascular proliferation. Treatment of other hyperproliferative disorders is also contemplated.

The term "advanced cancer" means cancer that is no longer localized to the primary tumor site, or a cancer that is Stage III or IV according to the American Joint Committee on Cancer (AJCC).

2.5. Treatment of Infectious Disease

Other methods of the invention are used to treat patients that have been exposed to pathogens. Similar to its application to tumors as discussed above, CTLA-4 antibody administered according to a dosage escalation regimen of the present invention can be used alone, or in combination with a vaccine to treat an infectious disease. CTLA-4 blockade has been shown to be effective in the acute phase of infections of *Nippostrongylus brasiliensis* (McCoy, K. et al. (1997) 186(2); 183-187) and *Leishmania donovani* (Murphy, M. et al. (1998) J. Immunol. 161:4153-4160). Examples of pathogens for which this therapeutic approach may be particularly useful include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus*, and *Pseudomonas aeruginosa*. CTLA-4 blockade is particularly useful in boosting immunity against established infections by agents such as HIV that present altered antigens over the course of the infections. These novel epitopes are recognized as foreign at the time of anti-human CTLA-4 administration, thus provoking a strong T-cell response that is not dampened by negative signals through CTLA-4.

Some examples of pathogenic viruses causing infections treatable by methods of the invention include hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme disease bacteria.

Some examples of pathogenic fungi causing infections treatable by methods of the invention include *Candida (albicans, krusei, glabrata, tropicalis*, etc.), *Cryptococcus neoformans, Aspergillus (fumigatus, niger*, etc.), *Genus Mucorales* (Mucor, Absidia, Rhizophus), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include Entamoeba histolytica, Balantidium coli, Naegleria fowleri, Acanthamoeba sp., Giardia lambia, Cryptosporidium sp., Pneumocystis carinii, Plasmodium vivax, Babesia microti, Trypanosoma brucei, Trypanosoma cruzi, Leishmania donovani, Toxoplasma gondi, Nippostrongylus brasiliensis.

2.6. Treatment for the Inappropriate Accumulation of Self-Antigens

A CTLA-4 antibody can be administered according to a dosage escalation regimen of the present invention to treat a patient having an inappropriate accumulation of self-antigens, such as amyloid deposits, cytokines such as TNFα, and IgE (for the treatment of allergy and asthma). For example, Alzheimer's disease involves inappropriate accumulation of Aβ peptide in amyloid deposits in the brain; antibody responses against amyloid are able to clear these amyloid deposits (Schenk et al., Nature 1999; 400:173-177).

2.7. Combination Treatments

2.7.1. CTLA-4 Antibodies and Vaccines for the Treatment of Cancer

According to the methods of the present invention, a CTLA-4 antibody can be administered in a dosage escalation regimen alone or in combination with one or more other therapeutic agents, or in conjunction with an immunotherapeutic vaccine for the tumor, such as chemotherapy, radiation therapy, cytokines, chemokines and other biologic signaling molecules, tumor specific vaccines, autologous and allogeneic stem cell rescue (e.g., to augment graft versus tumor effects), other therapeutic antibodies, molecular targeted therapies, anti-angiogenic therapy, infectious agents with therapeutic intent (such as tumor localizing bacteria), and gene therapy. The antibodies can be used in adjuvant or neo-adjuvant therapy, either alone or in conjunction with the aforementioned therapies.

Antibodies to CTLA-4 can be combined with an immunogenic agent, such as cancerous cells, purified tumor antigens (including recombinant proteins, peptides, and carbohydrate molecules), cells, and cells transfected with genes encoding immune stimulating cytokines and cell surface antigens such as B7 (see, e.g., Hurwitz, A. et al. (1998) Proc. Natl. Acad. Sci U.S.A. 1998; 95:10067-10071), or used alone, to stimulate immunity.

Treatment with a CTLA-4 antibody can be used to activate a pre-existing memory response in patients treated with a cancer vaccine. Thus, methods of this invention include treating vaccine-treated patients who are selected for further treatment with a CTLA-4 antibody to thereby further induce or enhance an immune response.

Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, *Cancer: Principles and Practice of Oncology*, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. Proc. Natl. Acad. Sci U.S.A. 1993; 90: 3539-43).

CTLA-4 blockade to boost GMCSF-modified tumor cell vaccines improves efficacy of vaccines in a number of experimental tumor models such as mammary carcinoma (Hurwitz et al., 1998, supra), primary prostate cancer (Hurwitz et al., Cancer Research 2000; 60:2444-8) and melanoma (van Elsas et al. J. Exp. Med. 1999, 190:355-66). In these instances, non-immunogenic tumors, such as the B16 melanoma, have been rendered susceptible to destruction by the immune system. The tumor cell vaccine may also be modified to express other immune activators such as IL-2, and costimulatory molecules, among others.

The study of gene expression and large scale gene expression patterns in various tumors has led to the definition of so called "tumor specific antigens" (Rosenberg, Immunity 1999; 10:281-7). In many cases, these tumor specific antigens are differentiation antigens expressed in the tumors and in the cell from which the tumor arose, for example melanocyte antigens gp100, MAGE, and Trp-2. More importantly, many of these antigens can be shown to be the targets of tumor specific T-cells found in the host. CTLA-4 blockade may be used as a boosting agent in conjunction with vaccines based on recombinant versions of proteins and/or peptides found to be expressed in a tumor. The tumor antigen may also include the protein telomerase, which is required for the synthesis of telomeres of chromosomes and which is expressed in more than 85% of human cancers and in only a limited number of somatic tissues (Kim et al., Science 1994; 266:2011-2013). These somatic tissues may be protected from immune attack by various means.

Tumor antigen may also be "neo-antigens" expressed in cancer cells because of somatic mutations that alter protein sequence or create fusion proteins between two unrelated sequences (i.e. bcr-abl in the Philadelphia chromosome), or idiotype from B-cell tumors. Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with CTLA-4 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot and Srivastava, Science 1995; 269:1585-1588; Tamura et al., Science 1997, 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al., Nature Medicine 1998; 4:328-332). DCs may also be transduced by genetic means to express these tumor antigens as well. DCs have also been fused directly to tumor cells for the purposes of immunization (Kugler et al., Nature Medicine 2000; 6:332-336). As a method of vaccination, DC immunization may be effectively boosted with CTLA-4 blockade according to a dosage escalation regimen of the present invention to activate more potent anti-tumor responses.

Another type of melanoma vaccine that can be combined with CTLA-4 blockade according to the present invention is a vaccine prepared from a melanoma cell line lysate, in conjunction with an immunological adjuvant, such as the MELACINE® vaccine, a mixture of lysates from two human melanoma cell lines plus DETOX™ immunological adjuvant. Vaccine treatment can be boosted with CTLA-4 antibody, with or without additional chemotherapeutic treatment.

2.7.2. Chemotherapeutic Agents and Other Standard Cancer Treatments

CTLA-4 administration in a dosage escalation regimen according to the present invention can be used in combination with standard cancer treatments. In these instances, it may be possible to reduce the dose of chemotherapeutic reagent administered (Mokyr et al., Cancer Research, 1998; 58:5301-5304). The scientific rationale behind the combined use of CTLA-4 blockade and chemotherapy is that cell death, that is a consequence of the cytotoxic action of most chemotherapeutic compounds, should result in increased levels of tumor antigen in the antigen presentation pathway. Thus, CTLA-4 can boost an immune response primed to chemotherapy release of tumor cells. Moreover, the immuno-stimulatory activity of CTLA-4 is useful to overcome the immunosuppressive effects of chemotherapy. Examples of chemotherapeutic agents with which CTLA-4 treatment can be combined include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (TAXOL®), pilocarpine, prochloroperazine, rituximab, tamoxifen, topotecan hydrochloride, trastuzumab, vinblastine, vincristine and vinorelbine tartrate. For prostate cancer treatment, a preferred chemotherapeutic agent with which CTLA-4 can be combined is paclitaxel (TAXOL®). For melanoma cancer treatment, a preferred chemotherapeutic agent with which CTLA-4 can be combined is dacarbazine (DTIC).

Other combination therapies that may result in immune system priming through cell death are radiation, surgery, and hormone deprivation (Kwon, E. et al. Proc. Natl. Acad. Sci U.S.A. 1999; 96 (26): 15074-9. Each of these protocols creates a source of tumor antigen in the host. For example, any manipulation of the tumor at the time of surgery can greatly increase the number of cancer cells in the blood (Schwartz, et al., Principles of Surgery 1984. $4^{th}$ ed. p.338). Angiogenesis inhibitors may also be combined with a CTLA-4 antibody dosage escalation regimen. Inhibition of angiogenesis leads to tumor cell death which may feed tumor antigen into host antigen presentation pathways.

2.7.3. Cytokines

A CTLA-4 antibody administered in a dosage escalation regimen according to the present invention can also be combined with other forms of immunotherapy such as cytokine treatment (e.g., interferons, GMCSF, GCSF, IL-2, or bispecific antibody therapy, which provides for enhanced presentation of tumor antigens (see e.g., Holliger (1993) *Proc. Natl. Acad. Sci. USA* 90:6444-6448; Poljak (1994) *Structure* 2:1121-1123).

Typical dosages regimens for cytokines include 720,000 IU/kg/dose every 8 hours for up to 15 doses per dosage of CTLA-4 antibody.

2.8. Pharmaceutical Compositions and Routes of Administration

The invention encompasses pharmaceutical compositions comprising a CTLA-4 human monoclonal antibody and/or a human sequence CTLA-4 antibody (intact or binding fragments) formulated together with a pharmaceutically acceptable carrier for use in a dosage escalation regimen. Some compositions include a combination of multiple (e.g., two or more) isolated human CTLA-4 antibodies and/or human sequence antibody or antigen-binding portions thereof of the invention.

Pharmaceutically acceptable carriers include solvents, dispersion media, coatings, antibacterial and antifungal agents (e.g., paraben, chlorobutanol, phenol sorbic acid, and the like), isotonic and absorption delaying agents, and the like that are physiologically compatible. The carrier can be suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

Pharmaceutically acceptable carriers also include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27). Supplementary active compounds can also be incorporated into the compositions.

Therapeutic compositions typically must be sterile, substantially isotonic, and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof, vegetable oils, such as olive oil, and injectable organic esters, such as ethyl oleate. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. These compositions may also contain adjuvants such as preservatives, wetting agents, emulsifying agents and dispersing agents.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A "pharmaceutically acceptable salt" refers to a salt that retains the desired biological activity of the parent compound and does not impart any undesired toxicological effects (See e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition for use in a dosage escalation regimen according to the present invention can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., *Sustained and Controlled Release Drug Delivery Systems*, J. R. Robinson, ed., Marcel Dekker, Inc., New York, 1978. In addition, prolonged absorption of an injectable pharmaceutical form may be brought about by the inclusion of agents which delay absorption such as aluminum monostearate and gelatin. Pharmaceutical compositions are preferably manufactured under GMP conditions.

Examples of pharmaceutically-acceptable antioxidants for use in pharmaceutical compositions include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations for use in the methods of the present invention include those suitable for oral, nasal, topical (including buccal and sublingual), rectal, vaginal and/or parenteral administration. The formulations can conveniently be presented in unit dosage form and may be prepared by any methods known in the art of pharmacy. The amount of active ingredient which can be combined with a carrier material to produce a single dosage form varies depending upon the subject being treated, and the particular mode of administration. Generally, out of one hundred percent, this amount ranges from about 0.01 percent to about ninety-nine percent of active ingredient, from about 0.1 percent to about 70 percent, or from about 1 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions can be administered with medical devices known in the art. For example, in a preferred embodiment, a therapeutic composition of the invention can be administered with a needleless hypodermic injection device, such as the devices disclosed in, e.g., U.S. Pat. Nos. 5,399,163, 5,383,851, 5,312,335, 5,064,413, 4,941,880, 4,790,824, or 4,596,556. Examples of implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known.

Some human sequence antibodies and human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, See, e.g., U.S. Pat. Nos. 4,522,811; 5,374,548; and 5,399,331. The liposomes may comprise one or more moieties which are selectively transported into specific cells or organs, thus enhance targeted drug delivery (See, e.g., V. V. Ranade (1989) *J. Clin. Pharmacol.* 29:685). Exemplary targeting moieties include folate or biotin (See, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); See also K. Keinanen; M. L. Laukkanen (1994) *FEBS Lett.* 346:123; J. J. Killion; I. J. Fidler (1994) *Immunomethods* 4:273. In some methods, the therapeutic compounds of the invention are formulated in liposomes; in a more preferred embodiment, the liposomes include a targeting moiety. In some methods, the therapeutic compounds in the liposomes are delivered by bolus injection to a site proximal to the tumor or infection. The composition should be fluid to the extent that easy syringability exists. It should be stable under the conditions of manufacture and storage and should be preserved against the contaminating action of microorganisms such as bacteria and fungi.

The present invention is further described by way of the following particular examples. However, the use of such examples is illustrative only and is not intended to limit the scope or meaning of the present invention or of any exemplified term. Furthermore, the present invention is not limited to any particular preferred embodiment(s) described herein. Indeed, many modifications and variations of the invention will be apparent to those skilled in the art upon reading this specification, and such "equivalents" can be made without departing from the invention in spirit or scope. The invention is therefore limited only by the terms of the appended claims, along with the full scope of equivalents to which the claims are entitled.

Example 1

Intra-Patient Dose Escalation of CTLA-4 Antibody in Patients with Metastatic Melanoma Forty-six HLA-A2 negative patients with progressive stage IV melanoma were treated using a CTLA-4 antibody dose escalation regimen to test whether higher doses of CTLA-4 antibody would induce increased autoimmunity and concomitant tumor regression. Twenty-three patients started CTLA-4 antibody administration at 3 mg/kg and 23 patients started treatment at 5 mg/kg. Each group was administered a dose every three weeks. Patients were administered the CTLA-4 antibody according to the dosage escalation regimen to a predetermined maximum dose of 9 mg/kg or until objective clinical responses or grade III/IV autoimmune toxicity was observed.

2.9. Methods 2.9.1. Patients and treatment

Patients eligible for treatment with CTLA-4 antibody (MDX-010, Medarex Inc., Bloomsbury, N.J.) were HLA-A*0201$^-$, had measurable stage IV melanoma, were at least 16 years of age, had a life expectancy of at least six months, an ECOG Performance Status≤2, and at least 3 weeks had elapsed since any systemic cancer therapy had been administered. Patients were excluded if they had autoimmune disease, active infection, were pregnant or nursing, had any concurrent medical condition requiring the use of systemic or topical steroids, or had received prior treatment with CTLA-4 antibody. All patients were treated on an Investigational Review Board approved protocol in the Surgery Branch, National Cancer Institute in Bethesda, Md.

At the initial patient screening, patients underwent a physical examination, assessment of performance status, ophthalmologic examination, ECG, pulmonary function tests, HLA typing, pheresis, rheumatoid factor, antinuclear antibody, human anti-human antibody (HAHA), hematologic, biochemical, and thyroid function tests. After every dose cycle, a physical exam and thyroid, hematologic, and biochemical panels were performed. Diagnostic imaging, an autoimmune panel, urinalysis, pheresis, and HAHA were obtained after every course, and a repeat ophthalmologic exam was performed after 4 cycles or as clinically indicated.

CTLA-4 antibody was administered to each patient in escalating doses until the development of an objective response (partial or complete), the predetermined maximum dose (i.e., 9 mg/kg) was reached, or a ≥ grade III autoimmune or another dose-limiting toxicity was observed. In the first 23 patients the starting dose of MDX-010 was 3 mg/kg, (this was also the initial dose reported in Attia et al., 2005 Sep. 1; 23(25):6043-53. Epub 2005 Aug. 8; and Phan et al., PNAS 2003, 100:8372-8377). Subsequent doses were escalated to 5 mg/kg, and then to 9 mg/kg. For the next 23 patients, the starting dose of CTLA-4 antibody was 5 mg/kg. A cycle was defined as one dose administration, and a course was defined as the administration of two doses at the same drug concentration.

Blood samples were drawn immediately prior to each dose cycle and again one hour post antibody infusion. Quantitative ELISA was used to determine plasma concentrations of CTLA-4 antibody as previously described. Briefly, microtiter plates were coated with recombinant human CTLA-4-Ig and bound CTLA-4 antibody was detected with an alkaline phosphatase labeled goat anti-human IgG probe. Phenotypic analysis of T-cell activation markers was performed using standard flow analysis techniques by Esoterix Inc. (East Windsor, N.J.) on peripheral blood samples obtained immediately prior to each course.

After completion of a course at a given dose, patients who did not experience an objective response or dose-limiting toxicity were escalated to the next dose level. Patients who experienced a complete response were treated for two additional cycles at the same dose level. Patients who achieved a partial response, and continued to have tumor regression, were re-treated at the same dose level until they achieved a complete response or no longer had tumor shrinkage. Once a patient experienced a complete response or the tumor size stabilized, they received two additional cycles at the same dose level. Patients who completed treatment with two cycles of antibody at each dose level, either 3 mg/kg, 5 mg/kg, and 9 mg/kg (patients 1-23), or 5 mg/kg and 9 mg/kg (patients 24-46), and had stable disease at follow-up evaluation were eligible to receive one additional course at 9 mg/kg. However, if these patients demonstrated progressive disease they were taken off of the study.

Patients who experienced non-skin related ≥ grade III adverse events, any autoimmune ocular toxicity, or required steroid therapy for toxicity attributable to CTLA-4 antibody administration did not receive further therapy, regardless of their clinical response status. Patients that experienced skin-related toxicity ≤ grade III, or a non-skin related toxicity < grade III may have had their antibody administration delayed.

The human IgG1κ CTLA-4 MDX-010 monoclonal antibody was administered as an intravenous bolus over 90 minutes every three weeks. Prior to antibody administration and, when possible, three weeks after each course, peripheral blood mononuclear cells (PBMC) were obtained by apheresis, isolated by Ficoll-Hypaque separation, and cryopreserved at −180 degrees Celsius in heat-inactivated human AB serum with 10% DMSO until further use.

2.9.2. Clinical Response Evaluation and on-Study Evaluation

All patients underwent computed axial tomography of the chest, abdomen, and pelvis, and MRI of the brain, within 28 days of starting treatment and after every two cycles of treatment. RECIST criteria were utilized to determine radiographic response to treatment (Therasse et al., J Natl Cancer Inst 2000, 92:205-216). The sum of the longest diameters of all tumors before and after therapy was calculated. A partial response was defined as a decrease of greater than or equal to 30% (but not 100%) of the sum of the longest diameters of index lesions, lasting at least one month with no growth of lesions or the appearance of new lesions. A complete response was defined as the disappearance of all lesions for greater than or equal to one month. Patients not achieving either a partial or complete response were deemed non-responders.

Forty-six HLA-A2 negative patients had stage IV melanoma with metastases to various sites (Table 1). Thirty-nine patients (85%) had visceral metastases. Thirty-two patients (70%) were male. Patients received treatment prior to enrollment in this study as follows: 29 (63%) had received chemotherapy, 14 (30%) radiation therapy, 2 (4%) hormonal therapy, 38 (83%) immunotherapy, and 28 (61%) had received more than one therapy. Patients 1-23 began treatment with CTLA-4 antibody at a concentration of 3 mg/kg and patients 24-46 started at a concentration of 5 mg/kg.

Treatment, autoimmunity, and response characteristics for patients treated with CTLA-4 antibody are summarized in Table 1.

TABLE 1

Patient characteristics, clinical response, and toxicity

| | Age | Sex | Disease Sites | Prior Therapy | Doses (mg/kg) | Response (mo.) * | Autoimmune Toxicity (Grade III/IV) ** |
|---|---|---|---|---|---|---|---|
| 1 | 47 | M | Mesenteric LN | S, I | 3, 3, 3, 3, 5, 5, 9, 9, 9, 9 | PR (12+) | hypophysitis |
| 2 | 50 | M | Cervical LN, lung, SQ | S, C, I | 3, 3 | NR | |
| 3 | 43 | M | Adrenal, ALN, lung | S, C, I | 3, 3, 5, 5, 9, 9, 9 | NR | hypophysitis |
| 4 | 66 | M | lung | S, I | 3, 3, 5, 5, 9, 9, 9, 9, 9, 9 | PR (12+) | |
| 5 | 30 | M | lung | S, I | 3, 3, 5, 5, 9 | NR | hypophysitis |
| 6 | 27 | F | ALN, brain, lung, RPLN, SQ, supraclavicular LN | R, S, I | 3, 3 | NR | |
| 7 | 48 | M | aortic LN, periportal LN, RPLN | S, C, I | 3, 3, 5, 5, 9, 9, 9, 9, 9, 9 | PR (11+) | |
| 8 | 33 | F | clavicular LN, liver, lung, MLN, mandibular LN, muscle | S, I | 3, 3, 5, 5 | NR | |
| 9 | 43 | M | ALN, MLN, liver, lung, periaortic LN, spleen, SQ | S, C, I | 3, 3, 5, 5, 9, 9 | NR | |
| 10 | 61 | M | lung, muscle | S, C, H, I | 3, 3, 5, 5, 9, 9 | PR (9) | hypophysitis |
| 11 | 34 | M | lung | S, I | 3, 3, 5, 5 | NR | |
| 12 | 43 | M | Iliac LN, periaortic LN | S, I | 3, 3, 5, 5, 9, 9 | NR | anterior uveitis |
| 13 | 63 | M | lung, MLN | S, C, I | 3, 3 | NR | |
| 14 | 68 | M | MLN, SQ | R, S, C, I | 3, 3, 5, 5, 9, 9 | NR | |
| 15 | 56 | F | bone, gallbladder, lung, muscle, popliteal LN, SQ | R, S | 3 | NR | dermatitis |
| 16 | 52 | F | lung | S, C, I | 3, 3, 5, 5, 9, 9 | NR | |
| 17 | 35 | F | adrenal, mesenteric LN, pelvis, RPLN | S, C, I | 3, 3, 5, 5, 9, 9, 9, 9 | NR | |
| 18 | 35 | M | liver, pelvis, SQ, spleen | S, C, I | 3, 3, 5 | NR | tubulointerstitial nephritis |
| 19 | 38 | M | bone, MLN, parotid, SQ | R, S, I | 3 | NR | |
| 20 | 66 | M | lung, MLN | R, S, I | 3, 3, 5, 5, 9, 9 | NR | |
| 21 | 44 | F | iliac LN, liver, lung, MLN, periaortic LN | S, I | 3, 3, 5, 5 | NR | arthritis |
| 22 | 64 | M | bone, liver, lung, MLN, SQ | S, C, I | 3, 3, 5, 5, 9, 9 | NR | |
| 23 | 48 | M | iliac LN, liver, MLN | S, C | 3, 3, 5, 5, 9, 9 | NR | diarrhea, hypophysitis |
| 24 | 40 | M | adrenal, ALN | S, C, I | 5 | NR | |
| 25 | 54 | M | bladder, kidney, liver, MLN, pancreas, RPLN, SQ | R, S, C, I | 5, 5, 9 | NR | |
| 26 | 44 | F | ALN, SQ | S, C, I | 5, 5 | NR | diarrhea |
| 27 | 46 | F | liver, lung, caval LN | R, S, C, I | 5, 5, 9, 9, 9 | NR | |
| 28 | 57 | F | liver, lung, MLN | S, C, I | 5, 5, 9, 9 | NR | |
| 29 | 52 | M | lung, RPLN, SQ | S, C, I | 5, 5, 9, 9 | NR | |
| 30 | 62 | F | iliac LN, lung | S, I | 5, 5, 9, 9, 9, 9, 9 | PR (6+) | diarrhea |
| 31 | 59 | M | liver, lung MLN | S | 5, 5, 9 | NR | diarrhea |
| 32 | 49 | M | lung, MLN | R, S, C, I | 5, 5, 9, 9 | NR | hypophysisis |
| 33 | 55 | F | bone, muscle, SQ | R, S, C | 5, 5, 9, 9 | NR | |
| 34 | 27 | M | internal mammary LN | R, S, C | 5, 5, 9, 9 | NR | |
| 35 | 55 | M | lung, SQ | S, C | 5, 5 | NR | hypophysisis |
| 36 | 57 | M | lung | S, C | 5, 5, 9, 9 | NR | |
| 37 | 59 | M | lung, MLN | S, C | 5, 5, 9, 9, 9, 9 | NR | hypophysisis |
| 38 | 35 | M | kidney, MLN | R, S, C, I | 5, 5, 9, 9 | NR | |
| 39 | 50 | M | liver, lung, pleura | S, I | 5, 5, 9, 9, 9 | NR | colitis |
| 40 | 24 | F | lung | R, S, C, I | 5, 9, 9 | NR | colitis, transaminitis |
| 41 | 67 | M | bone, breast, liver, lung, spleen, SQ | S, I | 5, 9, 9, 9, 9 | NR | |
| 42 | 49 | M | adrenal, clavicular LN, lung, pleura | S, I | 5, 5 | NR | dermatitis, diarrhea |
| 43 | 5 | M | ALN, MLN | S, I | 5, 5, 9, 9 | NR | |
| 44 | 41 | M | lung, RPLN, SQ | S, C, I | 5, 5, 9, 9 | NR | |
| 45 | 29 | F | ILN, lung, MLN | R, S, C, H, I | 5, 9, 9 | NR | |
| 46 | 46 | F | adrenal, MLN, SQ | R, S, C, I | 5, 5, 9 | NR | |

ALN, axillary lymph node; C, chemotherapy; CR, complete response; F, femal; H, hormonal therapy; I, immunotherapy; LN, lymph node; M, male; MLN, mediastinal lymph node; NR, no response, PR, partial response; R, radiation therapy; RP, retroperitoneal; S, surgery; SQ, subcutaneous
"+" indicates ongoing response
* Responses as of May 18, 2005
** including severe ocular toxicity

2.10. Results

2.10.1. Clinical Responses

Five of 46 patients (11%) (Table 1) satisfied criteria for objective clinical responses after treatment at 9 mg/kg (Table 2). To date, four of the five patients have ongoing responses, which have lasted over six months.

TABLE 2

Incidence of anti-tumor responses and autoimmunity in patients by dose level

| Dose | 3 mg/kg | 5 mg/kg | 9 mg/kg | all doses |
|---|---|---|---|---|
| Responders | 0 | 0 | 5 | 5/46 (11%) |
| Grade III/IV or severe ocular autoimmunity | 1 | 5 | 12 | 18/46 (39%) |
| Responders with autoimmunity | 0 | 0 | 3 | 3* |

*p = 0.37, Fisher's Exact Test comparing responders with autoimmunity to nonresponders with autoimmunity Patient 1 achieved an objective partial response in lymph nodes of the retroperitoneum, pre-aortic, and peri-pancreatic areas after receiving MDX-010 at four doses of 3 mg/kg, two doses of 5 mg/kg, and two doses of 9 mg/kg. Patient 1 received a final course of 9 mg/kg before experiencing hypophysitis and, to date, remains a responder at over 12 months. Patient 4 experienced regression of multiple lung metastases after two doses of MDX-010 each at 3 mg/kg, 5 mg/kg, and 9 mg/kg without grade III/IV autoimmune toxicity. Patient 4 received two additional courses at 9 mg/kg and, to date, remains a partial responder for over 12 months. Patient 7 achieved complete regression of peri-portal and peri-pancreatic lymph nodes, and partial regression of a peri-aortic lymph node after two doses of MDX-010 each at 3 mg/kg, 5 mg/kg, and 9 mg/kg without grade III/IV autoimmune toxicity. Patient 7 received two additional courses at 9 mg/kg and, to date, remains a responder at over 11 months. Patient 10 experienced complete regression of an intramuscular lesion and partial responses in multiple lung lesions after receiving two doses of MDX-010 each at 3 mg/kg, 5 mg/kg, and 9 mg/kg. Patient 10 remained a partial responder for nine months before growth of new lung lesions. Patient 30 achieved a partial response in an iliac lymph node and a lung lesion after receiving two doses of MDX-010 at 5 mg/kg, and 4 doses at 9 mg/kg. Patient 30 received an additional dose at 9 mg/kg before experiencing grade III autoimmune diarrhea and, to date, remains a partial responder at over six months.

2.10.2. Autoimmune Effects

Eighteen patients (39%) experienced 21 grade III/IV autoimmune events or severe ocular toxicity requiring steroid treatment (Tables 1 and 2). These events consisted of: anterior uveitis (1), arthritis (1), colitis/diarrhea (7), dermatitis (2), hypophysitis (8), transaminitis (1), and tubulointerstitial nephritis (1) (Tables 1 and 3). Of these 18 patients who experienced severe autoimmune toxicity, 3 (17%) were objective clinical responders, whereas of the 28 patients who did not experience severe autoimmunity, 2 (17%) were responders (p=0.37, Fisher's Exact Test). In addition, 10 patients experienced 11 grade I/II autoimmune events including alopecia areata (1), anterior uveitis/episcleritis (1), arthritis (1), diarrhea (3), dermatitis (4), and hypopigmentation (1) (Table 3). Five of these patients had concurrent grade III/IV autoimmune toxicity. Thus, 23 patients experienced autoimmunity at any grade. Analysis of these patients resulted in 4/23 (17%) of patients with autoimmunity that experienced tumor regression, and 1/23 (4%) of patients without autoimmunity that experienced tumor regression (p=0.35, Fisher's Exact Test).

TABLE 3

Number of autoimmune toxicities by severity

| Toxicity | Grade I/II | Grade III/IV |
|---|---|---|
| alopecia areata | 1 | 0 |
| anterior uveitis | 1 | 1 |
| arthritis | 1 | 1 |
| colitis/diarrhea | 3 | 7 |
| dermatitis | 4 | 2 |
| hypophysitis | 0 | 8 |
| hypopigmentation | 1 | 0 |
| transaminitis | 0 | 1 |
| tubulointerstitial nephritis | 0 | 1 |
|  | 11 | 21 |

2.10.3. Pharmacokinetics

Peripheral blood samples were obtained immediately prior to antibody administration and one hour post-infusion from patients who began treatment at 3 mg/kg of CTLA-4 antibody in order to analyze the effect of increasing antibody doses on both peak and trough plasma levels of the antibody. Trough levels increased proportionally from below detection levels to 68.9 ug/mL with increasing doses and concentrations of CTLA-4 antibody. Similarly, peak levels increased proportionally from 55.8 ug/mL to 356.3 ug/mL with increasing doses and concentrations of antibody, though levels appeared to stabilize with repeated dosing at 9 mg/kg (Table 4). Plasma concentrations of CTLA-4 antibody measured before and after doses of 3 mg/kg were comparable to peak and trough plasma concentrations from patients treated on previous protocols where patients received antibody doses of 3 mg/kg.

TABLE 4

Pharmacokinetics of CTLA-4 antibody administration

| Sample Timepoint | N | PK concentration (ug/mL) |
|---|---|---|
| pre-treatment | 13 | BD |
| post 3 mg/kg × 1 | 5 | 55.8 ± 6.1 |
| pre 3 mg/kg × 2 | 3 | 17.4 ± 2.9 |
| post 3 mg/kg × 2 | 2 | 116.2 ± 15.4 |
| pre 5 mg/kg | 4 | 25.5 ± 1.3 |
| post 5 mg/kg × 1 | 3 | 131.5 ± 66.8 |
| pre 5 mg/kg × 2 | 4 | 29.6 ± 9.3 |
| post 5 mg/kg × 2 | 3 | 193.1 ± 30.7 |
| pre 9 mg/kg | 10 | 48.0 ± 4.9 |
| post 9 mg/kg × 1 | 3 | 287.0 ± 109.8 |
| pre 9 mg/kg × 2 | 5 | 60.0 ± 12.4 |
| post 9 mg/kg × 2 | 3 | 366.4 ± 28.6 |
| pre 9 mg/kg × 3 | 5 | 63.7 ± 8.6 |
| post 9 mg/kg × 3 | 4 | 342.8 ± 68.2 |
| pre 9 mg/kg × 4 | 2 | 68.9 ± 7.3 |
| post 9 mg/kg × 4 | 3 | 356.3 ± 74.2 | reported as the mean concentration ± the standard error of the mean
BD = below detection

2.10.4. Phenotypic Changes

Using flow cytometry, pre- and post-treatment peripheral blood samples were analyzed for changes in surface expression of T-cell activation markers (Table 5). Samples were obtained immediately prior to each course (three weeks after the prior course of treatment) in order to analyze the effect of increasing antibody doses on the activation of T-cells. Peripheral blood was stained for both CD3 and CD4 surface expression. Patients for whom a pre-treatment sample and at least one post-treatment course sample was available were used for analysis, including three of the five responders. CD25+ surface expression decreased significantly on CD4+ cells after 5 mg/kg and 9 mg/kg. HLA-DR expression increased significantly both on CD4+ and CD8+ cells. CD69 expression trended towards a decrease on both CD4+ and CD8+ cells, while CD45RO+ expression increased on both CD4+ and CD8+ cells.

TABLE 5

Flow cytometric analysis of selected T-cell surface markers in peripheral blood of patients receiving escalating doses of anti-CTLA-4 antibody

| | Mean % Δ | | |
|---|---|---|---|
| N | 0 to 3 mg/kg 18 | 0 to 5 mg/kg 24 | 0 to 9 mg/kg 12 |
| CD25+ (% CD3 + CD4+) | −0.5 | −4.7 | −6.8 |
| p-value | 0.8 | 0.006 | 0.03 |
| HLA-DR+ (% CD3 + CD4+) | +10.1 | +10.7 | +13.2 |
| p-value | 0.0002 | <0.0001 | 0.0001 |
| HLA-DR+ (% CD3 + CD4−) | +11.0 | +8.5 | +11.5 |
| p-value | 0.01 | 0.002 | 0.003 |
| CD69+ (% CD3 + CD4+) | −11.2 | −5.6 | −10.5 |
| p-value | 0.04 | 0.1 | 0.1 |
| CD69+ (% CD3 + CD4−) | −12.8 | −11.4 | −18.6 |
| p-value | 0.01 | 0.004 | 0.007 |
| CD45RO+ (% CD3 + CD4+) | +3.9 | +5.7 | +9.8 |
| p-value | 0.02 | 0.0005 | 0.007 |
| CD45RO+ (% CD3 + CD4−) | +6.0 | +4.2 | +7.0 |
| p-value | 0.03 | 0.06 | 0.04 | two-tailed p-value using paired T-test

Five of the 46 patient treated with MDX-010 administered in an escalating dosage regimen exhibited a response to the regimen. Of these 5 patients, 2 patients exhibited a response without grade III/IV autoimmune toxicity, and 1 of these 2 patients had tumor regression without autoimmune toxicity. These results show the therapeutic effectiveness and tolerability of an escalating dosage regimen of a CTLA-4 antibody.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein, including all patents, published patent applications, published scientific articles, protocols, and GenBank Accession Numbers are incorporated by reference in their entireties for all purposes.

The invention claimed is:

1. A method for treating prostate cancer in a patient comprising administering a CTLA-4 antibody to the patent according to a dosage escalation regimen, which comprises: (a) administering a first CTLA-4 antibody dosage of about 3 mg/kg and then administering one or more increased dosages of the CTLA-4 antibody to the patient until the dosage results in a complete response in the patient; and (b) when the patient experiences a complete response, administering two additional cycles of the CTLA-4 antibody at the dosage level that resulted in the complete response, wherein a complete response is disappearance of the measurable prostate tumor for greater than or equal to one month, wherein the CTLA-4 antibody comprises a heavy chain variable region that comprises CDR1, CDR2, and CDR3 domains; and a light chain variable region that comprises CDR1, CDR2, and CDR3 domains, wherein the heavy chain variable region CDR1 comprises amino acids having the sequence set forth in SEQ ID NO:1; the heavy chain variable region CDR2 comprises amino acids having the sequence set forth in SEQ ID NO:2; the heavy chain variable region CDR3 comprises amino acids having the sequence set forth in SEQ ID NO:3; the light chain variable region CDR1 comprises amino acids having the sequence set forth in SEQ ID NO:4; the light chain variable region CDR2 comprises amino acids having the sequence set forth in SEQ ID NO:5; and the light chain variable region CDR3 comprises amino acids having the sequence set forth in SEQ ID NO:6.

2. The method of claim 1, wherein each one of the two additional cycles comprises one administration of a CTLA-4 antibody dosage.

3. The method of claim 1, wherein the dosage escalation regimen comprises a linear increase in CTLA-4 antibody dosage.

4. The method of claim 3, wherein the dosage escalation regimen comprises administering a first CTLA-4 antibody dosage of about 3 mg/kg, a second CTLA-4 antibody dosage of about 5 mg/kg, and a third CTLA-4 antibody dosage of about 9 mg/kg.

5. The method of claim 1, wherein the dosage escalation regimen comprises a stepwise increase in CTLA-4 antibody dosage.

6. The method of claim 5, wherein the dosage escalation regimen comprises administering an increased CTLA-4 antibody dosage every six weeks.

7. The method of claim 5 or 6, wherein the dosage escalation regimen comprises administering a first CTLA-4 antibody dosage of about 3 mg/kg, a second CTLA-4 antibody dosage of about 3 mg/kg, a third CTLA-4 antibody dosage of about 5 mg/kg, a fourth CTLA-4 antibody dosage of about 5 mg/kg, and a fifth CTLA-4 antibody dosage of about 9 mg/kg.

8. The method of claim 1, comprising administering a CTLA-4 dosage every three weeks.

9. The method of claim 1, further comprising administering a vaccine to the patient.

10. The method of claim 9, wherein the vaccine comprises gp100, tyrosinase, MART-1 or a combination thereof.

11. The method of claim 1, further comprising administering a chemotherapeutic agent to the patient.

12. The method of claim 1, further comprising administering a cytokine to the patient.

13. The method of claim 12, wherein the cytokine is IL-2.

14. The method of claim 1, wherein the CTLA-4 antibody comprises a heavy chain variable region comprising amino acids comprising the sequence set forth in SEQ ID NO:7; and a light chain variable region comprising amino acids comprising the sequence set forth in SEQ ID NO:8.

15. A method for treating prostate cancer in a human patient comprising administering a CTLA-4 antibody to the patient according to a dosage escalation regimen, which comprises: (a) administering a first CTLA-4 antibody dosage of about 5 mg/kg and then administering one or more increased dosages of the CTLA-4 antibody, to the patient until the dosage results in a complete response in the patient; and (b) when the patient experiences a complete response, administering two additional cycles of the CTLA-4 antibody at the dosage level that resulted in the complete response, wherein a complete response is disappearance of the measurable prostate tumor for greater than or equal to one month, wherein the CTLA-4 antibody comprises a heavy chain variable region that comprises CDR1, CDR2, and CDR3 domains; and a light chain variable region that comprises CDR1, CDR2, and CDR3 domains, wherein the heavy chain variable region CDR1 comprises amino acids having the sequence set forth in SEQ ID NO:1; the heavy chain variable region CDR2 comprises amino acids having the sequence set forth in SEQ ID NO:2; the heavy chain variable region CDR3 comprises amino acids having the sequence set forth in SEQ ID NO:3; the light chain variable region CDR1 comprises amino acids having the sequence set forth in SEQ ID NO:4; the light chain variable region CDR2 comprises amino acids having the sequence set forth in SEQ ID NO:5; and the light chain variable region CDR3 comprises amino acids having the sequence set forth in SEQ ID NO:6.

16. The method of claim 15, wherein the dosage escalation regimen comprises a linear increase in CTLA-4 antibody dosage.

17. The method of claim 15, wherein the dosage escalation regimen comprises a stepwise increase in CTLA-4 antibody dosage.

18. The method of claim 16, wherein the dosage escalation regimen comprises administering a first CTLA-4 antibody dosage of about 5 mg/kg and a second CTLA-4 antibody dosage of about 9 mg/kg.

19. The method of claim 17, wherein the dosage escalation regimen comprises administering an increased CTLA-4 antibody dosage every six weeks.

20. The method of claim 17 or 19, wherein the dosage escalation regimen comprises administering a first CTLA-4 antibody dosage of about 5 mg/kg, a second CTLA-4 antibody dosage of about 5 mg/kg, and a third CTLA-4 antibody dosage of about 9 mg/kg.

21. The method of claim 15, comprising administering a CTLA-4 antibody dosage every three weeks.

22. The method of claim 15, further comprising administering a vaccine to the patient.

23. The method of claim 22, wherein the vaccine comprises gp100, tyrosinase, MART-1 or a combination thereof.

24. The method of claim 15, further comprising administering a chemotherapeutic agent to the patient.

25. The method of claim 15, further comprising administering a cytokine to the patient.

26. The method of claim 25, wherein the cytokine is IL-2.

27. The method of claim 15, wherein each one of the two additional cycles comprises one administration of a CTLA-4 antibody dosage.

28. The method of claim 15, wherein the CTLA-4 antibody comprises a heavy chain variable region comprising amino acids comprising the sequence set forth in SEQ ID NO:7; and a light chain variable region comprising amino acids comprising the sequence set forth in SEQ ID NO:8.

* * * * *